(12) United States Patent
Cannon et al.

(10) Patent No.: US 6,620,595 B2
(45) Date of Patent: Sep. 16, 2003

(54) RETROVIRAL VECTORS COMPRISING AN ENHANCED 3' TRANSCRIPTION TERMINATION STRUCTURE

(75) Inventors: Paula Marie Cannon, Altadena, CA (US); Maria Barcova, Studio City, CA (US)

(73) Assignee: University of Southern California, Los Angeles, CA (US)

(*) Notice: Subject to any disclaimer, the term of this patent is extended or adjusted under 35 U.S.C. 154(b) by 0 days.

(21) Appl. No.: 09/855,159

(22) Filed: May 14, 2001

(65) Prior Publication Data

US 2002/0042136 A1 Apr. 11, 2002

Related U.S. Application Data

(60) Provisional application No. 60/203,884, filed on May 12, 2000.

(51) Int. Cl.[7] .................. C12P 21/00; C07H 21/04; C12M 15/867
(52) U.S. Cl. ................... 435/70.1; 435/320.1; 536/24.1
(58) Field of Search ............................ 435/320.1, 70.1; 536/24.1

(56) References Cited

PUBLICATIONS

Cannon et al., Retroviral vectors for gene therapy, 2000, Gene Therapy, pp. 1–16.*
Miyoshi et al., Development of a self–inactivating lentivirus vector, 1998, Journal of Virology, p. 8150–8157.*
Zufferey et al., Self–inactivating lentivirus vector for safe and efficient in vivo gene delivery, 1998, Journal of Virology, p. 9873–9880.*
International Search Reported dated Feb. 27, 2002.
Dougherty, et al., "A Promoterless Retroviral Vector Indicates that there are Sequences in U3 Required for 3' RNA Processing," *Proc. Natl. Acad. Sci. USA*, 84:1197–1201 (Mar. 1987).
Brackenridge, et al., "Transcription and polyadenylation in a short human intergenic region," *Nucleic Acids Research*, 25(12):2326–2335 (1997).
Carswell, et al., "Efficiency of utilization of the simian virus 40 late polyadenylation site: Effects of upstream sequences," *Mol. Cell. Biol.*, 9(10):4248–4258 (Oct. 1989).
Cherrington, et al., "Upstream sequences and cap proximity in the regulation of polyadenylation in ground squirrel hepatitis virus," *J. Virol.*, 66(12):7589–7599 (Dec. 1992).
Cooke, et al., "Utilization of splicing elements and polyadenylation signal elements in the coupling of polyadenylation and last–intron removal," *Mol. Cell. Biol.*, 19(7):4971–4979 (Jul. 1999).
DeZazzo, et al., "Relative roles of signals upstream of AAUAAA and promoter proximity in regulation of human immunodeficiency virus type 1 mRNA 3' end formation," *Mol. Cell. Biol.*, 12(12):5555–5562 (Dec. 1992).

DeZazzo, et al., "Sequences upstream of AAUAAA influence poly(A) site selection in a complex transcription unit," *Mol. Cell. Biol.*, 9(11):4951–4961 (Nov. 1989).
Gilmartin, et al., "Activation of HIV–1 pre–mRNA 3' processing in vitro requires both an upstream element and TAR," *The EMBO Journal*, 11(12):4419–4428 (1992).
Graveley, et al., "A common mechanism for the enhancement of mRNA 3' processing by U3 sequences in two distantly related lentiviruses," *J. Virol.* 70(3):1612–1617 (Mar. 1996).
Ismail, et al., "Use of intron–disrupted polyadenylation sites to enhance expression and safety of retroviral vectors," *J. Virol.*, 75(1):199–204 (Jan. 2001).
Iwakuma, et al., "Self–inactivating lentiviral vectors with U3 and U5 modifications," *Virology*, 261:120–132 (1999).
Lutz, et al., "Direct interaction of the U1 snRNP–A protein with the upstream efficiency element of the SV40 late polyadenylation signal," *Genes & Development*, 8:576–586 (1994).
Moreira, et al., "Upstream sequence elements enhance poly(A) site efficiency of the C2 complement gene and are phylogenetically conserved," *The EMBO Journal*, 14(15):3809–3819 (1995).
Moreira, et al., "The upstream sequence element of the C2 complement poly(A) signal activates mRNA 3' end formation by two distinct mechanisms," *Genes & Development*, 12:2522–2534 (1998).
Prescott, et al., "Sequence elements upstream of the 3' cleavage site confer substrate strength to the adenovirus L1 and L3 polyadenylation sites," *Mol. Cell. Biol.*, 14(7):4682–4693 (Jul. 1994).
Russnak, R., "Regulation of polyadenylation in hepatitis B viruses: stimulation by the upstream activating signal PS1 is orientation–dependent, distance–independent, and additive," *Nucleic Acids Research*, 19(23):6449–6456 (Nov. 6, 1991).
Russnak, et al., "Sequences 5' to the polyadenylation signal mediate differential poly(A) site use in hepatitis B viruses," *Genes & Development*, 4:764–776 (1990).

(List continued on next page.)

*Primary Examiner*—James Ketter
*Assistant Examiner*—Daniel M. Sullivan
(74) *Attorney, Agent, or Firm*—J. Timothy Meigs; Douglas A. Golightly; George C. Jen

(57) ABSTRACT

The invention provides novel retroviral vectors that have enhanced transcription termination structures. The termination structures comprise one or several heterologous upstream transcription termination enhancer (UE) sequences, or one or more additional copies of endogenous UE sequences operably associated with the 3' LTR polyadenylation signal. The retroviral vectors of the invention have various improved properties over conventional vectors, including stronger gene expression, enhanced vector titer and reduced interference with host cell gene expression resulting from read-through of vector initiated transcriptional events.

31 Claims, 12 Drawing Sheets

OTHER PUBLICATIONS

Sanfaçon, et al., "A dissection of the cauliflower mosaic virus polyadenylation signal," *Genes & Development*, 5:141–149 (1991).

Schek, et al., "Definition of the upstream efficiency element of the simian virus 40 late polyadenylation signal by using in vitro analyses," *Mol. Cell. Biol.*, 12(12):5386–5393 (Dec. 1992).

Valsamakis, et al., "Elements upstream of the AAUAAA within the human immunodeficiency virus polyadenylatoin signal are required for efficient polyadenylation in vitro," *Mol. Cell. Biol.*, 12(9):3699–3705 (Sep. 1992).

Valsamakis, et al., "The human immunodeficiency virus type 1 polyadenylation signal: A 3' long terminal repeat element upstream of the AAUAAA necessary for efficient polyadenylation," *Proc.Natl. Acad. Sci. USA*, 88:2108–2112 (Mar. 1991).

* cited by examiner

FIG. 3
A. Split packaging helper constructs
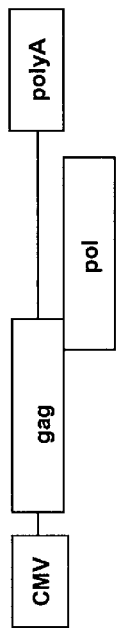
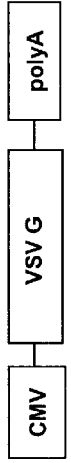
B. SIN vector
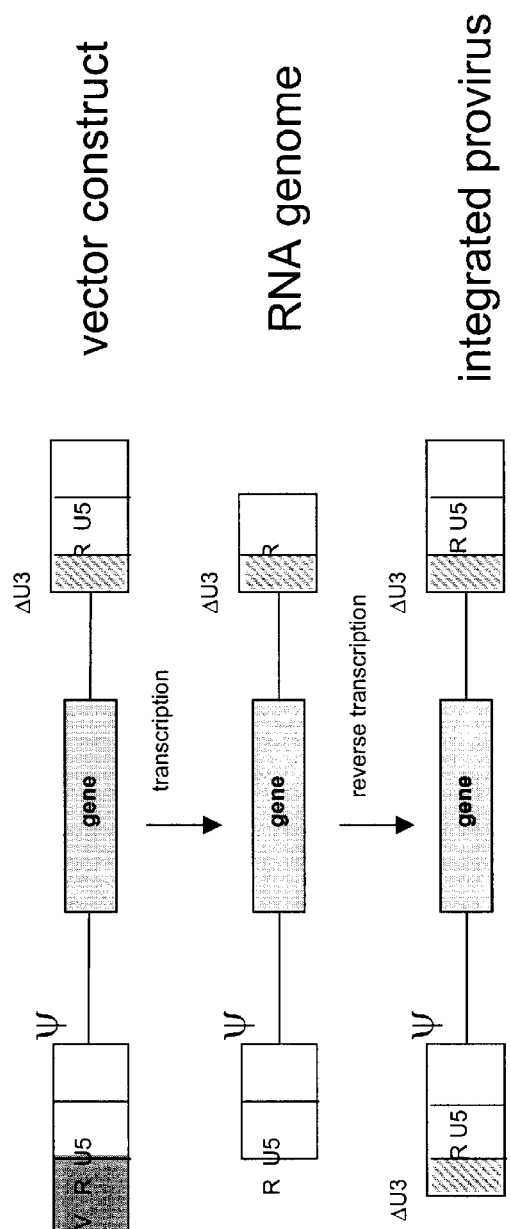

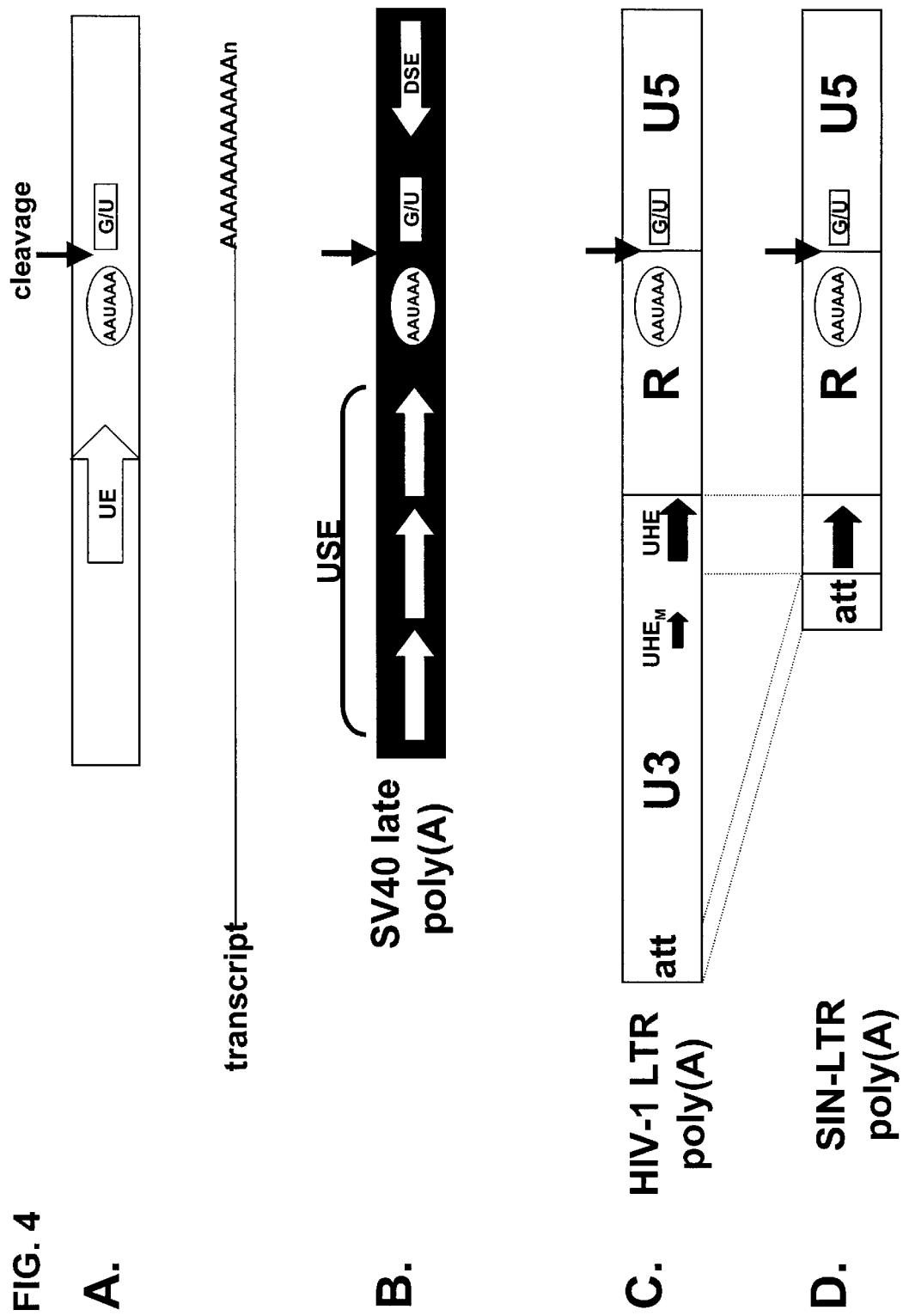

FIG. 5

Human immunodeficiency virus type 1 UE (UHE)
CAGCTGCTTTTTGCCTGT...76nt...

SV40 UE (USE)
TTTATTTGTGAAATTTGTGATGCTATTGCTTT ATTTGTAACCATTATAAGCTGC

Equine infectious anemia virus UE
TTTGTGACGCGTTAAGTTCCTGTTTTACAGTATTATAAGTACTTGTGTTCTGACAATT...56nt...

Cauliflower mosaic virus UE
TGTGTGAGTAGTTCCCAGATAAGGGAATTAGGGTTCTTATAGGGTTTCGCTCATGTGTTGAGCAT
ATAAGAAACCCTAGTATGATTTGTATTTGTA...13nt...

Ground squirrel hepatitis virus UE
TCATGTATCTTTTTCACCTGTGCCTTGTTTTGCCTGTGTTCCATGTCCTACTGTT...51nt...

Adenovirus L3 UE
CCACTTCTTTTTGTCACTTGAAAAACATGTAAAAATAATGTACTAGGAGACACTTT

Human complement C2 UE
TTGACTGACTCATGCTTGTTTCACTTTCACATGGAATTTCCCAGTTATGAAATT

Human lamin B2 UE
ATTCGGTTTTAAGAAGATGCATGCCTAACGTGTTCTTTTTTTCCAATGATTGTAATATACA
TTTATGACTGGAAACTTTTT...12nt...

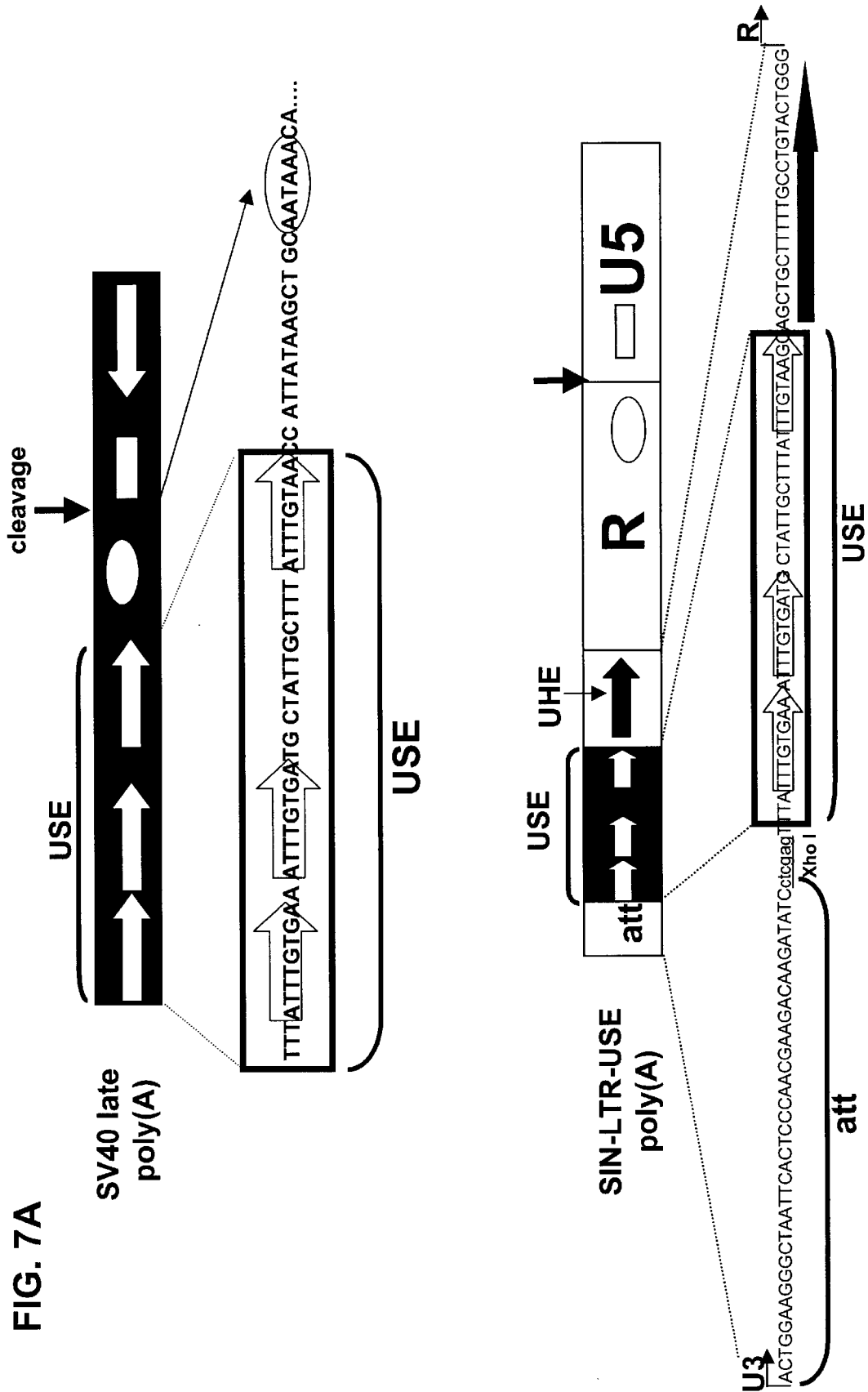

RETROVIRAL VECTORS COMPRISING AN ENHANCED 3' TRANSCRIPTION TERMINATION STRUCTURE

This application claims the benefit under 35 USC §119(e) of U.S. provisional patent application Ser. No. 60/203,884, filed May 12, 2000, for "Retroviral Vectors Comprising An Enhanced 3' Transcription Termination Structure." The disclosure of this provisional application is incorporated herein by reference in its entirety.

FIELD OF THE INVENTION

The present invention relates to retroviral vectors. The invention particularly relates to retroviral vectors that have an enhanced 3' transcription termination structure and to methods for using such vectors to express heterologous coding sequences in mammalian cells and organisms.

BACKGROUND OF THE INVENTION

Retroviral Vectors

Retroviral vectors are currently one the most frequently used gene delivery vehicles in gene therapy protocols. Fundamental to the utility of retroviral vectors is the various retrovirus characteristics retained by the vectors. Such characteristics include efficient transfection of many cell types and stable integration of their genomes into a host cell chromosome, which enables long-term expression of vector encoded genes. Another important retained characteristic is that the initial steps of the vector life cycle from binding of vector particles through integration of its genome into a host cell's genetic material require no de novo synthesis of viral proteins.

Basic Components of Retroviral Vectors

The main features of the wild-type retroviral genome are summarized in FIG. 1, which shows the open reading frames and the structures of the viral long terminal repeats (LTRs). Retroviral vectors comprise genomes derived from retroviruses. The simplest type of retroviral vectors have a significantly pared down retroviral genome which is missing most of the sequences encoding viral genes (e.g., gag, env and pol) and retains only sequences that are required for the packaging, reverse transcription and integration. The pared down retroviral genomes are often referred to as retroviral backbones, upon which further modifications can be made and to which heterologous genes and sequences can be added to form retroviral vectors. Typically, a heterologous gene is inserted into the backbone in such a way that allows the 5' LTR promoter to drive its subsequent expression. An expression construct comprising a heterologous gene operatively associated with a promoter can also be inserted into the backbone for delivery and expression in a target cell.

Retroviral vectors missing some or all of the viral genes are replication deficient. Production of viral particles comprising such vectors requires vector propagation in host cells that provide the missing functions in trans. Trans complementation can be achieved in various ways including transfecting the host cell with a packaging helper construct, also derived from a retroviral genome, which expresses the missing viral proteins but cannot be packaged because of a deletion of the packaging signal. This system of retroviral vector production is illustrated in FIG. 2. When both the vector and packaging helper construct are present in a producer cell, infectious retroviral particles are released that are capable of delivering the vector genome with its inserted gene. This process of gene delivery is referred to as transduction.

Lentiviral Vectors

To date, the most common retroviral vectors used in clinical gene therapy protocols have been based on the murine leukemia virus (MuLV), and a variety of packaging systems to enclose the vector genome within viral particles have been developed (reviewed in Miller, A D. 1997. Development and applications of retroviral vectors. In Retroviruses, Ed. Coffin J M, Hughes S H, Varmus H E. CSHL Press, New York.). The vectors themselves have all of the viral genes removed, are completely replication-defective, and can accept up to approximately 6–8 kb of exogenous DNA. These current vector/packaging systems seem to pose minimal risk to patients, and to date there have been no reports of toxicity or long-term problems associated with their use.

However, MuLV and vectors derived from it are only able to infect dividing cells. This is because the pre-integration nucleoprotein complex is unable to cross an intact nuclear membrane. In contrast, the prototypical lentivirus HIV-1 has been shown capable of nuclear import even when an intact membrane exists, and HIV-1-derived vectors are therefore able to transduce non-dividing cells (Naldini et al., Science 272:263–267 (1996)). This property of HIV vectors makes them particularly attractive candidates for gene therapy when the target cell is non-dividing and stable integration of the heterologous gene is required.

Improvements in Retroviral Vector Design and Production Systems

The retroviral vector production system described above is functional but unsatisfactory in several ways. In particular, overlaps that remain between the vector sequences and sequences encoding viral components in packaging helper constructs means that there is a significant risk of recombination events that would create an infectious replication-competent retrovirus (RCR). Such overlaps exist largely because extensive sequences of the gag gene are retained in the vector to enhance packaging efficiency. In addition, the LTRs are frequently retained in packaging helper constructs to provide both promoter and polyadenylation sequences.

In order to minimize the risk of RCR production, various improved approaches to vector design and production have been developed. One approach splits the packaging components, placing the gag-pol genes and the env gene onto separate plasmids that can be individually introduced into the packaging cell. In another approach, Env-mediated recombination is avoided by the use of heterologous envelope proteins whose coding sequences have no homology with the genome of the parental retrovirus but which can be incorporated into the vector particle (a process referred to as pseudotyping). A commonly used heterologous envelope protein is VSV G, the G protein from vesicular stomatitis virus (Burns et al., Proc. Natl. Acad. Sci. 90:8033–8037 (1993)). See FIG. 3, Panel A.

In yet another approach, LTR-mediated recombination is reduced by the use of heterologous promoters and polyadenylation signals in the packaging helper constructs. This can also have the advantage of enhancing vector titer (Soneoka et al., Nucleic Acids Res 25:628–633 (1995)). This approach typically involves deleting non-essential sequences from the vector LTRs and where appropriate, replacing the deleted sequences with heterologous sequences. For example, heterologous promoters, such as the CMV immediate-early promoter, have been used to replace the 5' U3 promoter. In other instances, 3' U3 sequences have been significantly deleted, as is the case with self-inactivating (SIN) vectors, as long as the integrase recognition sequences (i.e., att sequences) are retained (Yu et al., Proc. Natl. Acad. Sci 83:3194–3198 (1986)). See FIG. 3., Panel B.

These approaches have been used in developing various lentivirus-based vectors, which raise special safety concerns because of the possibility of pathogenic RCR arising from recombination events. Example products of this approach include the CMV-driven SIN vectors (Zufferey et al., J. Virol. 72:9873–9880 (1988)), the minimal packaging helper constructs with all of the non-essential genes inactivated or removed (Zufferey et al., Nat. Biotechnol. 15:871–875 (1997)), and retroviral particles comprising non-HIV-1 envelope proteins such as the VSV G.

Retroviral Vector Integration

Retroviral vectors integrate their genomes into a host cell's genetic material. A great deal is known about the process of retroviral integration, which is carried out by the viral integrase. Integrase recognizes sequences at the ends of the LTRs of the DNA provirus (the att sites, FIG. Panel 1B), and inserts the provirus more or less randomly into the host genome, although some sequence preferences have been reported (Carteau et al., J. Virol. 72:4005–4014 (1988)).

The ability of retroviral vectors to integrate is a two-edged sword. On the one hand, it allows for the possibility of stable long-term expression of vector encoded genes, with the integrated provirus being passed on to all daughter cells. On the other hand, vector integration can interfere with the normal functioning of flanking host genes. Indeed, retroviruses were first identified on the basis of their ability to cause oncogenic transformation. One type of interference is the inappropriate activation of host genes by read-through transcription, i.e. the continuation of viral transcripts past the 3' LTR transcription termination site and into downstream host gene sequences. Read-through transcription from proviruses into host sequences has been observed for several retroviruses (R. V. Gunataka Microbiol. Rev. 57:511–521 (1993); Bohnlein et al., J. Virol. 63:421–424 (1989); Herman et al., Science. 236:845–848 (1987); Iwasaki et al., Genes & Dev. 4.2299–2307 (1990); Cherrington et al. EMBO J. 11:1513–1524 (1992)). Recent evidence shows that integrated HIV-1 provirus can also effect read-through transcription of flanking host cell sequences (Dron et al., Arch Virol. 144:19–28 (1999)).

Transcription Termination of mRNAs

The 3' end of messenger RNAs (mRNAs) transcribed by RNA polymerase II is created by cleavage of the nascent transcript. This event occurs predominantly at a polyadenylation site and is followed by the template-independent addition of an approximately 250-nucleotide poly(A) tail (Wahle et al., FEMS Microbiol. Rev. 23:277–295 (1999)). It has been suggested that the poly(A) tail influences many aspects of mRNA metabolism, including stability, translational efficiency, and transport of processed mRNA from the nucleus to the cytoplasm (Lewis et al., Microbiol Mol Biol Rev. 63:405–445 (1999); Colgan et al., Genes & Dev. 11:2755–2766 (1997); Huang et al., Mol. Cel. Biol. 16:1534–1542 (1996); Sachs et al., J. Biol. Chem. 268: 22955–22958 (1993)). A strong polyadenylation signal has been observed to increase the level of precursor cleavage and the length of poly (A) of mRNA produced in vitro (Lutz et al., Genes & Dev. 10:325–337 (1996)). In one instance, increased poly (A) tail length correlates with enhanced transgene expression (Loeb et al., 1999 West Cost Retrovirus Meeting, abstract p57).

Polyadenylation Signals

The core polyadenylation signal consists of two recognition elements flanking a cleavage/polyadenylation site. A highly conserved AAUAAA hexanucleotide element (Proudfoot et al., Nature 263:211–214 (1976)) is located 8 to 31 nucleotides upstream of the cleavage site (Chen et al., Nucleic Acid Res. 23:2614–2620 (1995)) and a poorly conserved GU— or U-rich (G/U-rich) downstream element is located 14 to 70 nucleotides downstream of the AAUAAA element. Cleavage of the mRNA transcript usually occurs after an A residue, with a preference for a CA dinucleotide, between these two elements (Sheets et al., Nucleic Acid Res. 18:5799–5805 (1990))(FIG. 4).

A growing number of polyadenylation signals have also been shown to contain additional elements located upstream of the AAUAAA sequence that enhance transcription termination (FIG. 4). Early examples of such upstream enhancers (UEs) were found in the polyadenylation signals of various viruses, including HIV-1 (Valsamakis et al., Mol. Cell. Biol. 12:3699–3705 (1992); Gilmartin et al., EMBO J. 11:4419–4428 (1992)), equine infectious anemia virus (Graveley et al., J. Virol. 70:1612–1617 (1996)), simian virus 40 (SV40) (Carswell et al., Mol. Cell. Biol. 9:4248–4258 (1989)), adenovirus (Prescott et al., Mol. Cell. Biol. 14:4682–4693 (1994); DeZazzo et al., Mol. Cell. Biol. 9:4951–4961 (1989)), cauliflower mosaic virus (Sanfacon et al., Genes & Dev. 5:141–149 (1991)), and ground squirrel hepatitis virus (Cherrington et al., J, Virol. 66:7589–7596 (1992)) poly(A). More recently, UEs have also been identified in the polyadenylation signals of mammalian genes, such as the human complement C2 gene (Moreira et al., EMBO J. 14:3809–3819 (1995); Moreira et al., Genes & Dev. 12:2522–2534 (1998)) and the lamin B2 gene (Brackenridge et al., Nucleic Acid Res. 25:2326–2335 (1997)).

In general, UEs comprise U- or UG-rich sequences, but there is no clear sequence homology between different UEs (Carswell et al., Mol. Cell. Biol. 9:4248–4258 (1989); R. H. Russnak, Nucleic Acid Res. 19:6449–6456 (1991); Sanfacon et al., Genes & Dev. 5:141–149 (1991); Moreira et al., EMBO J. 14:3809–3819 (1995)) (FIG. 5). Notwithstanding the absence of sequence homology, certain viral UEs appear functionally interchangeable (Russnak et al., Genes & Dev. 4:764–776 (1990); Valsamakis et al., Proc Natl Acad Sci USA. 88:2108–2112 (1991); Graveley et al., J. Virol. 70:1612–1617 (1996)).

The UE of the SV40 late polyadenylation signal (also known as USE) is located 13–51 nucleotides upstream of the MUAM element (FIG. 5) (Schek et al., Mol Cell Biol. 12:5386–5393 (1992); Lutz et al., Genes & Dev. 8:576–586 (1994); Carswell et al., Mol. Cell. Biol. 9:4248–4258 (1989); Cooke et al., Mol Cell Biol. 19:4971–4979 (1999)). The USE plays an important role in enhancing the activity of the core polyadenylation signal as USE mutations reduced polyadenylation efficiency by 75 to 85%, both in vitro and in vivo (Carswell et al., Mol. Cell. Biol. 9:4248–4258 (1989); Schek et al., Mol. Cell. Biol. 12:5386–5393 (1992)). Within the USE, three core U-rich elements with the consensus sequence AUUUGUPuA have been identified as the active components. They apparently function in a distance-dependent manner, and when present in multiple copies, in an additive manner on polyadenylation efficiency (Carswell et al., Mol. Cell. Biol. 9:4248–4258 (1989)). The UE of the ground squirrel hepatitis virus polyadenylation signal also influences the activity of the core polyadenylation signal in a orientation-dependent, additive but distance-independent manner (R. H. Russnak, Nucleic Acid Res. 19:6449–6456 (1991)).

Retroviral Polyadenylation Signals

Retroviral 5' and 3' LTRs contain a polyadenylation signal AAUAAA in the R region, a G/U-rich downstream element is located in the U5 region and the cleavage/polyadenylation site defines the R/U5 boundary (FIG. 4). In HIV-1, the 3'

LTR has an UE (also known as UHE) in the U3 region, 77–94 nucleotides upstream of the AAUAAA motif (FIG. 4, Panel C, and FIG. 5). The UHE significantly increases the processing efficiency of the 3' LTR polyadenylation signal (DeZazzo et al. Mol Cell Biol. 12:5555–5562 (1991); Valsamakis et al., Mol Cell Biol. 12:3699–3705 (1992)). A putative minor polyadenylation enhancer, designated $UHE_M$, has also been identified 146–171 nucleotides upstream of the AAUAAA motif (Valsamakis et al., Proc Natl Acad Sci USA. 88:2108–2112 (1991)) (FIGS. 4 & 5).

Despite the presence of the AAUAAA and G/U-rich downstream elements at both the 5' and 3' LTRs, the HIV-1 polyadenylation signal copied from the 3' LTR is preferentially recognized. Several mechanisms have been proposed to account for the differential recognition of the two polyadenylation signals (Das et al., J. Virol. 73:81–91 (1999); Cherrington et al., J, Virol. 66:7589–7596 (1992); DeZazzo et al., Mol Cell Biol. 12:5555–5562 (1992); J. Cherrington, EMBO J. 11:1513–1524 (1992)).

BRIEF SUMMARY OF THE INVENTION

The present invention relates to retroviral vectors that have an enhanced 3' transcription termination structure. In one embodiment, retroviral vectors of the invention comprise one or more heterologous upstream enhancer (UE) sequences operably associated with the 3' LTR polyadenylation signal. In another embodiment, retroviral vectors of the invention comprise additional copies of endogenous UE sequences operably associated with the 3' LTR polyadenylation signal. The invention provides compositions comprising such retroviral vectors, their nucleotide sequences, viral particles produced by such vectors, and cells comprising such vectors and their proviral sequences. The invention also provides methods for using such retroviral vectors for expressing heterologous coding sequences in mammalian cells and organisms.

The present invention is based on the surprising discovery that incorporating one or more heterologous UE sequences, or one or more additional copies of endogenous UE sequences into retroviral vectors increased the transcriptional termination efficiency of their 3' LTR, and that vectors having such modification produced higher vector titers (i.e., titers of viral particles comprising the vector) than those produced by otherwise identical vectors having no such modifications. While not intending to be limited to any theory, it is believed that enhancing transcriptional termination by the 3' LTR increases the production, stability, nuclear export and/or translation of vector mRNA, and that such increases lead to higher vector RNA production and/or gene expression, and hence the higher vector titers in producer cells.

Definitions

Unless otherwise specified herein, the following words and terms shall have the following meanings with respect to the present disclosure and the appended claims.

"3' LTR" refers to a 3' retroviral long terminal repeat, which may or may not be modified from its corresponding native (i.e., that existing in the wild-type retrovirus) 3' LTR by deleting and/or mutating endogenous sequences and/or adding heterologous sequences.

"5' LTR" refers to a 5' retroviral long terminal repeat, which may or may not be modified from its corresponding native 5' LTR by deleting and/or mutating endogenous sequences and/or adding heterologous sequences.

"3' LTR polyadenylation signal" refers to the polyadenylation signal present in the 3' LTR of retroviruses.

"Upstream enhancer" and "UE" are used interchangeably, and refer to a control element present in the 3' untranslated region of various eukaryotic and viral genes that enhances transcriptional termination by a polyadenylation signal located downstream of the enhancer. Examples of UEs are found in the SV40 late polyadenylation signal (USE), the HIV-1 LTR (UHE) and the ground squirrel hepatitits virus (UGE).

"Upstream enhancer sequence" and "UE sequence" are used interchangeably, and refer to the sequence of a UE or an active segment thereof. Like a UE, an active segment of a UE increases the transcriptional termination activity of a polyadenylation signal when it is placed 5' upstream of that signal. A UE may comprise many active segments that may or may not be overlapping in sequence.

In the context of the retroviral vectors of the invention, a "heterologous" UE sequence is a UE sequence from a UE not identical to the one present in the native 3' LTR of the retrovirus from which the retroviral vector of the invention is derived. By contrast, an "endogenous" UE sequence is a UE sequence from a UE present, such as UHE of HIV-1, in the native 3' LTR of the retrovirus from which the retroviral vector of the invention is derived.

"3' transcription termination structures" of a retroviral vector refer to structures within and proximal to the 3' LTR that effect termination of transcriptions initiated upstream of the structures. Such structures comprise the 3' LTR polyadenylation signal and may additionally comprise endogenous UE sequences and heterologous UE sequences operatively associated with that signal.

"Polynucleotide" refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

"Producer cell" refers to a cell that comprises a retroviral vector or its proviral sequence and produces transducing particles comprising the retroviral vector. Where the retroviral vector is replication deficient, the producer cell complements the deficiency by producing the required replication function(s) in trans.

"Retrovirus" denotes a class of viruses that use RNA-directed DNA polymerase, or "reverse transcriptase" to copy a viral RNA genome into a double-stranded DNA intermediate which integrates into the chromosomal DNA of a host cell. Retroviruses include lentiviruses. Examples of retroviruses include, but are not limited to, Moloney murine leukemia virus, spleen necrosis virus, Rous sarcoma virus, Harvey sarcoma virus, avian leukosis virus, human immunodeficiency virus, myeloproliferative sarcoma virus, and mammary tumour virus. Examples of lentiviruses include human immunodeficiency virus, simian immunodeficiency virus, equine infectious anemia virus, feline immunodeficiency virus, visna virus.

"Vector" refers to "retroviral vector," unless otherwise specified.

"Retroviral vector genome" refers to a polynucleotide comprising sequences from a retroviral genome that are sufficient to allow an RNA version of that polynucleotide to be packaged into a retroviral particle, and for that packaged RNA polynucleotide to be reverse transcribed and integrated into a host cell chromosome by the action of the retroviral enzymes, such as reverse transcriptase and integrase, contained in the retroviral particle.

"Gene" refers to a polynucleotide that encodes a polypeptide.

"Coding sequence" refers to a polynucleotide that encodes a polypeptide, antisense RNA, a ribozyme or a structural RNA, such as snRNA, tRNA and rRNA.

In the context of the retroviral vectors of the invention, a "heterologous" gene or coding sequence is a gene or coding sequence that is not identical to any gene or coding sequence found in the retrovirus from which the retroviral vector of the invention is derived.

Two genes or sequences are "identical" if the order of nucleotides in each gene or sequence is the same, without any addition, deletion or material substitution.

In the context of polynucleotides, a "sequence" is an order of nucleotides in a polynucleotide in a 5' to 3' direction in which residues that neighbor each other in the sequence are contiguous in the primary structure of the polynucleotide.

"Operatively associated" refers to a juxtaposition of genetic elements, wherein the elements are in a relationship permitting them to operate in the expected manner. For example, a UE sequence is operatively linked to a polyadenylation signal in the same DNA molecule if the UE sequence enhances transcriptional termination by that signal. Similarly, a promoter is operatively associated with a coding region in the same DNA molecule if the promoter enables transcription of the coding sequence. There may be intervening residues between such associated elements so long as their functional relationship is maintained.

Panel A. The basic organization of a simple C-type retrovirus is shown. The Long Terminal Repeats (LTRs) contain promoter and polyadenylation sequences that are preferentially used at the 5' and 3' LTRs respectively. Both full-length and spliced transcripts are produced, which code for three major proteins; Gag and Gag-Pol are translated from the full-length transcript and Env is translated from the spliced transcript. The full-length transcript also serves as the RNA genome. At the 5' region of the genome is a packaging signal (ψ) that is necessary for the incorporation of the genome into viral particles. SD, splice donor; SA, splice acceptor.

Panel B. The LTRs comprise three regions, designated U3, R and U5. The promoter and enhancer sequences are active in the 5' LTR only and are located in the U3 region, while the polyadenylation site in the 3' LTR defines the R/U5 boundary. The aft sequences at the ends of the LTRs are necessary for integration.

Figure 1:
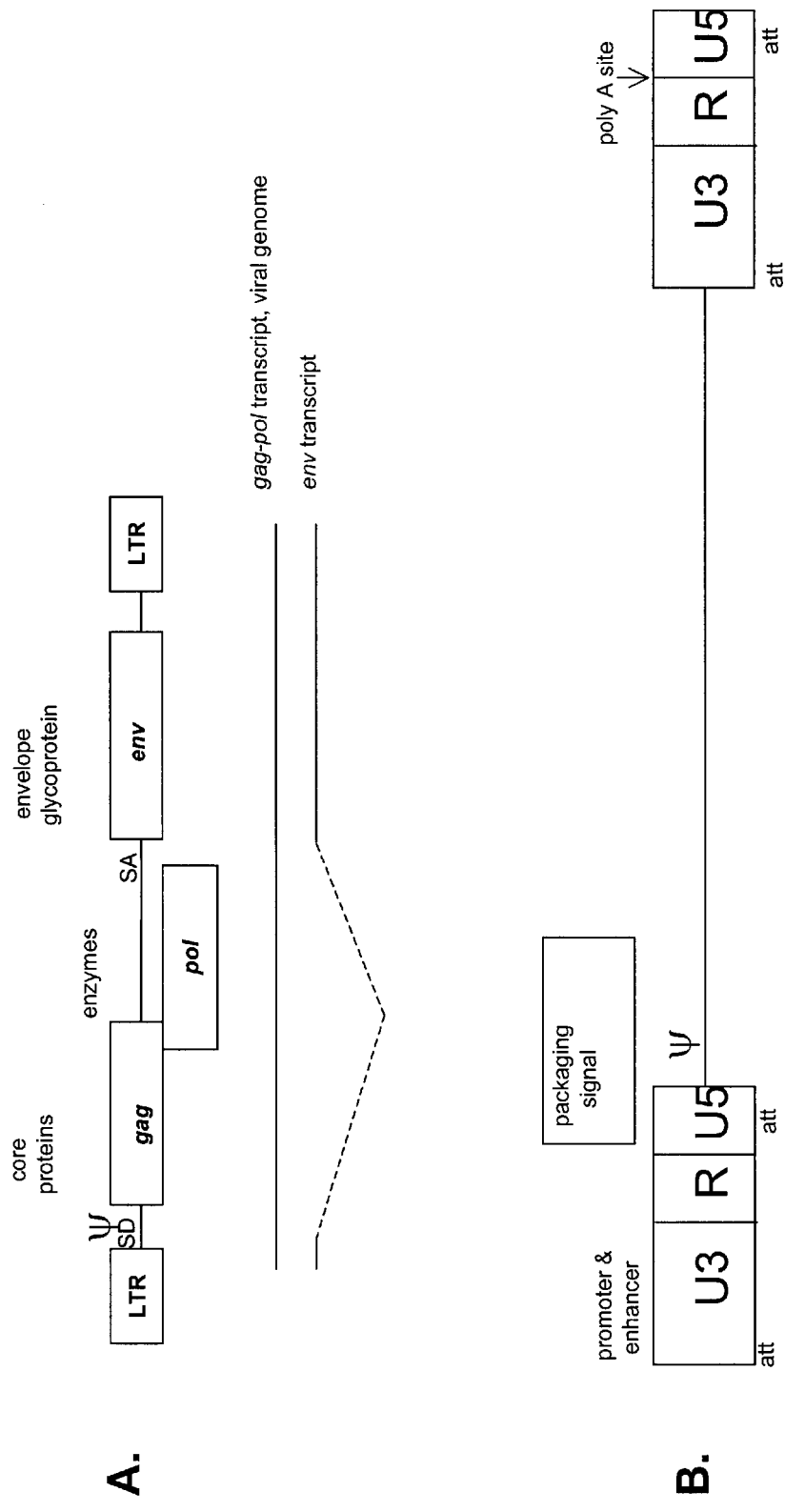
FIG. 1: Retroviral Genome Organization.
Figure 2:
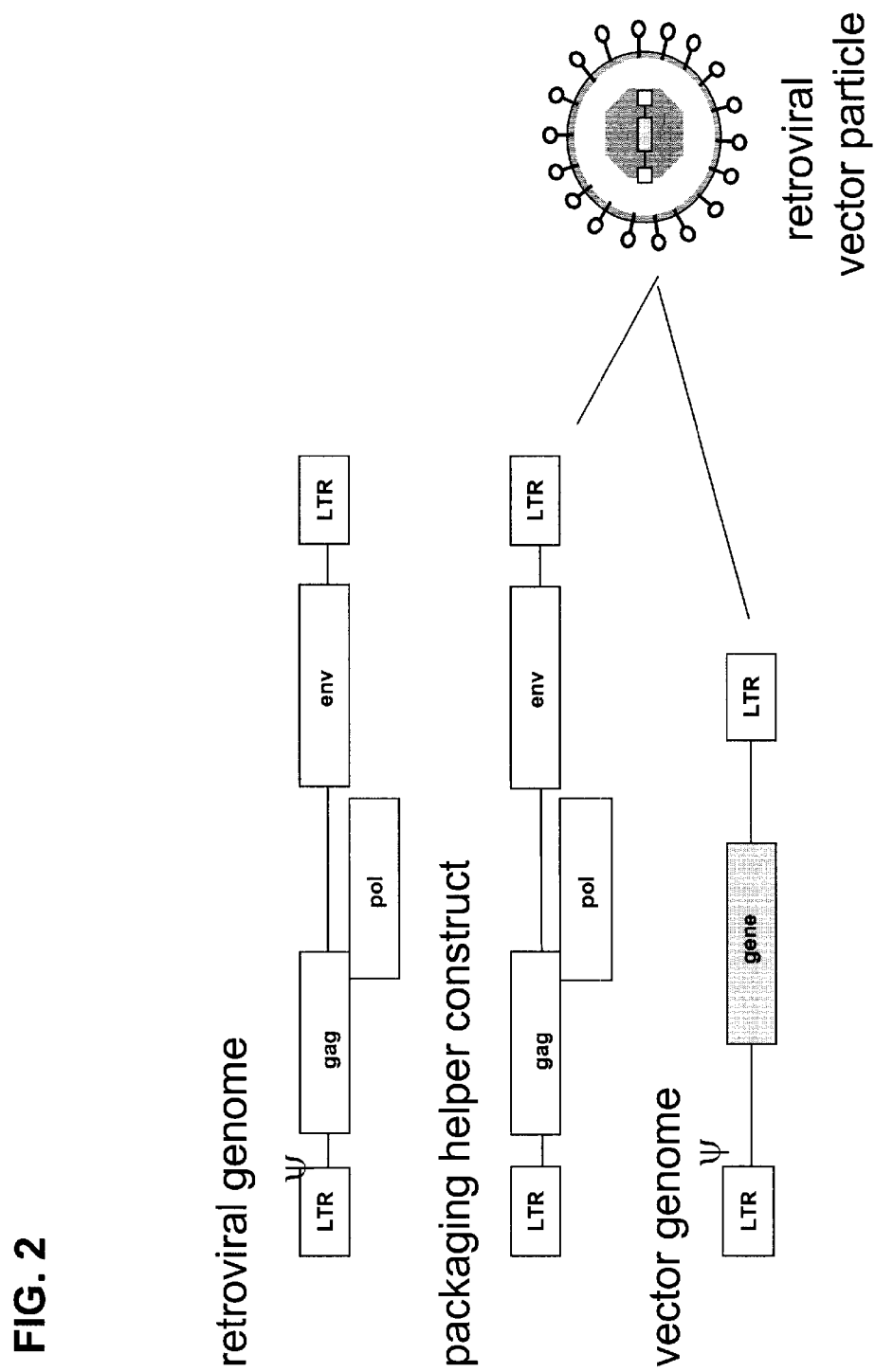

FIG. 2. Production of Replication Defective Retroviral Vector Particles. The genomes of wild-type retrovirus, packaging helper construct and replication defective retroviral vector as shown at the top, middle and bottom of the figure, respectively. The packaging helper construct provides all of the viral proteins in trans to the vector genome which codes for no viral proteins but retains all of the necessary cis elements for packaging and integration. The deletion of the packaging signal from the packaging helper construct prevents its incorporation into vector particles.

FIG. 3. Improvements in Retroviral Vector Design.

Panel A. Split Packaging Helper Constructs. Sequences encoding Gag-Pol and Env proteins are separated onto two different plasmids and safety is further increased by the use of an heterologous fusion protein (e.g. VSV G protein). Expression is maximized from the packaging helper construct through the use of a non-LTR promoter (e.g., the human CMV promoter).

Panel B. SIN Vectors. The U3 promoter sequences at the 5' LTR are replaced by a CMV promoter and the U3 promoter at the 3' LTR are minimized by deletion. Following reverse transcription, the deleted U3 sequences (AU3) are copied into both the 5' and 3' LTRs of the provirus, resulting in greatly reduced promoter activity from the integrated vector 5' LTR. This is the basis of self-inactivating (SIN) vectors.

FIG. 4 Polyadenylation Signal: Role of Upstream Enhancer (UE)

Panel A. Model for UE-mediated enhancement of polyadenylation efficiency. The core polyadenylation signal consists of two elements: the AAUAAA hexanucleotide and a G/U-rich element and cleavage occurs between these two elements.

Panel B. SV40 late polyadenylation signal contains an upstream enhancer (UE, a/k/a USE), and a downstream enhancer (DSE). The 40 nucleotide long USE is composed of 3 nearly identical elements (arrows) having the sequence AUUUGUPuA. The USE is located −15 to −54 nucleotide relative to the AAUAAA motif.

Panel C. Schematic representation of full-length HIV-1 LTR. The AAUAAA element is located in the R region, 19 nucleotides upstream of the cleavage/polyadenylation site that defines the R/U5 boundary. The G/U-rich sequence is located in the U5 region. An endogenous upstream element (UHE) is located in the U3 region, 77–94 nucleotides upstream of the AAUAAA motif. A putative minor upstream element sequence ($UHE_M$) is located 146–171 nucleotides upstream of the AAUAAA signal. Panel D. Schematic representation of self-inactivating (SIN) HIV-1 LTR. The HIV-1 core polyadenylation elements and the UHE are preserved in the SIN-LTR, created by a 395 nucleotide deletion of the promoter within the U3 region. The remaining U3 sequences contain 38 nucleotides at the 5' end which includes the integrase attachment site (aft) and a 23 nucleotide region at the 3' boundary of U3 that includes the 18 nucleotide-long UHE (see also FIG. 7A).

FIG. 5. Examples of Upstream Enhancers (UE).

Human immunodeficiency virus type 1 UHE (SEQ ID NO:11); SV40 USE (SEQ ID NO:1); equine infectious anemia virus UE (SEQ ID NO:2); cauliflower mosaic virus UE (SEQ ID NO:5); ground squirrel hepatitis virus UGE (SEQ ID NO:6); adenovirus L3 UE (SEQ ID NO:8); human complement C2 UE (SEQ ID NO:9); lamin B2 UE (SEQ ID NO:10). The distance of the 3' end of each UE (shown in the box) to the 5' end of the AAUAAA signal (represented by the ellipse) are indicated. The 14nt between the 3' end of the SV40 USE (SEQ ID NO:1) and the 5' end of the AAUAAA signal are set forth as SEQ ID NO:13.

Figure 6:
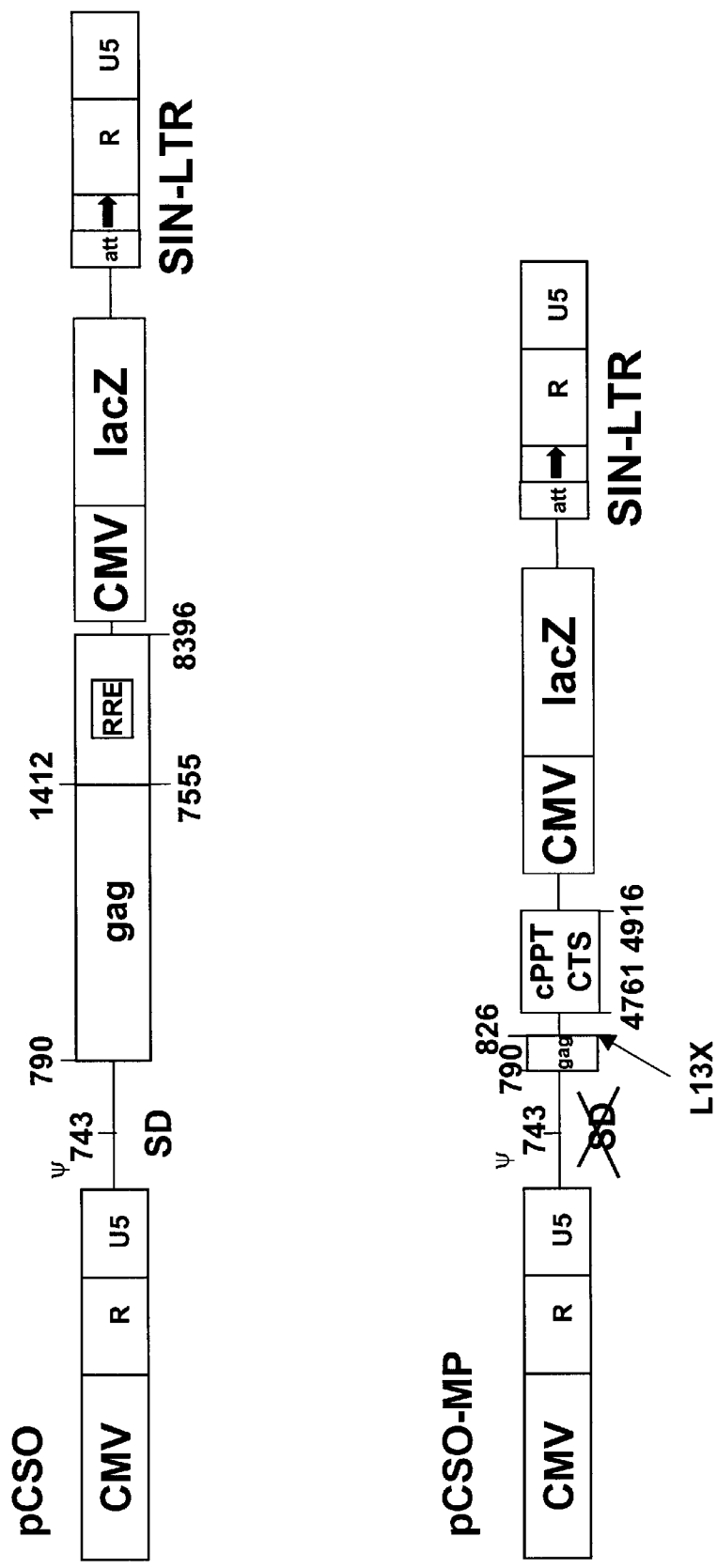
Figure 7B:
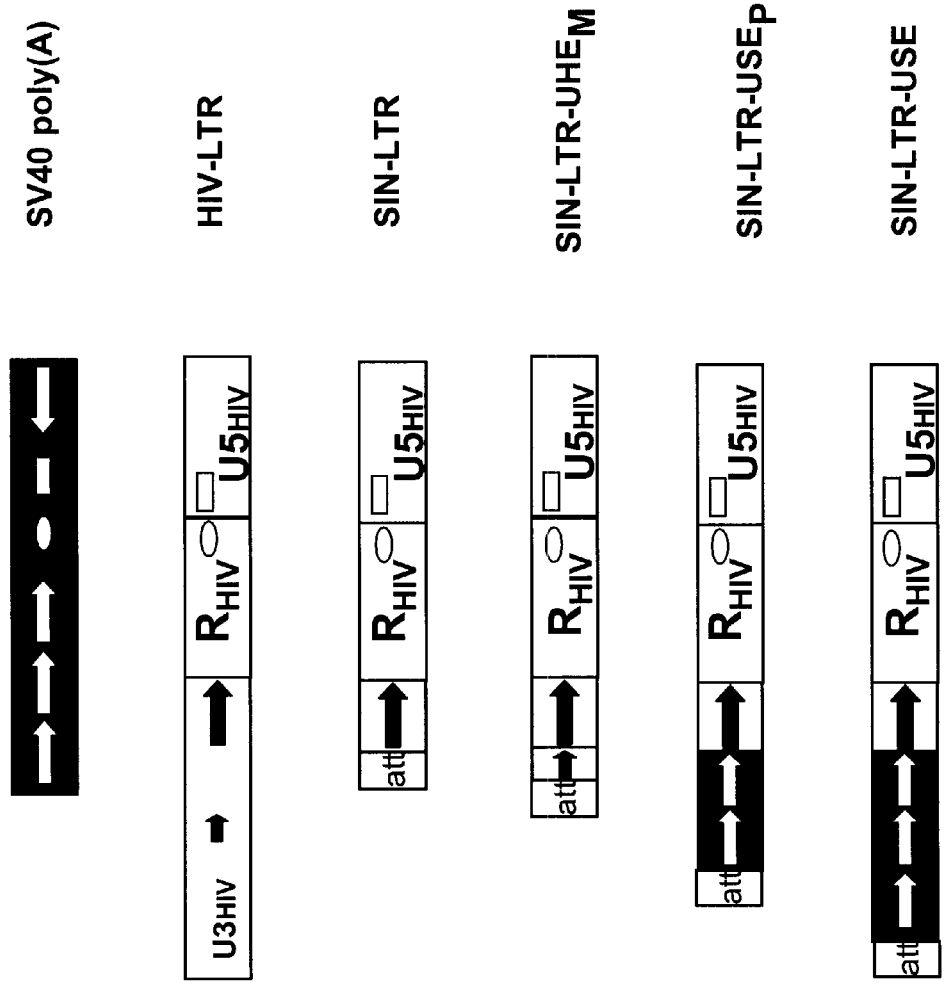

FIG. 6. Minimal SIN Vectors.

pCSO is a SIN retroviral vector comprising a lentivirus backbone. It contains 2100 nucleotides of HIV-1 genome.

pCSO-MP is derived from pCSO and the HIV-1 sequences have been reduced to 835 nucleotides. The env sequence including the RRE site has been deleted, and the extent of gag sequence has been considerably reduced. All splice sites have been deleted. The $13^{th}$ codon of gag is mutated to a stop codon (L13X) and the central polypurine tract-central termination sequence (cPPT/CTS) is inserted to increase the efficiency of reverse transcription. Nucleotide numbering of these vectors is based on pNL4-3 sequence. FIGS. 7A & 7B. Engineering of SIN-LTRs with Enhanced Transcription Termination Structures.

FIG. 7A. SIN-LTR-USE.

The structures of SV40 late polyadenylation signal are shown in the black background and SEQ ID NO:14. The structures of SIN 3' LTR are shown in the white background.

The 40 nucleotide SV40 upstream enhancer (USE) was inserted into the LTR between the att site and the HIV LTR upstream enhancer (UHE). This sequence is set forth as SEQ ID NO:15.

FIG. 7B. Schematic representation of various configurations of SIN LTRs with engineered transcription termination structures. The structures of SV40 late polyadenylation signal are shown in the black background. The structures of SIN 3' LTR are shown in the white background. The structures of ground squirrel hepatitis virus are shown as hatched. Constructs SIN-LTR-UHE$_M$, SIN-LTR-USE$_P$ and SIN-LTR-USE contain inserts of USE sequences or an endogenous putative UE sequence. The SIN-LTR-UHE$_M$ contains a 27 nucleotide insert of the minor HIV-1 putative UE (UHE$_M$) (short black arrow). Construct SIN-LTR-USE contains the complete 40 nucleotide long USE from the SV40 late polyadenylation signal, composed of 3 identical AUUUGUPuA elements (white arrows). SIN-LTR-USE$_P$ contains a 20 nucleotide segment of the USE, containing two AUUUGUPuA elements (white arrows). Construct SIN-LTR-UGE contains the complete 56 nucleotide long UGE sequence from ground squirrel hepatitis virus. The ellipse represents the AAUAAA signal. The small rectangle represents the G/U-rich downstream element.

Figure 8A:
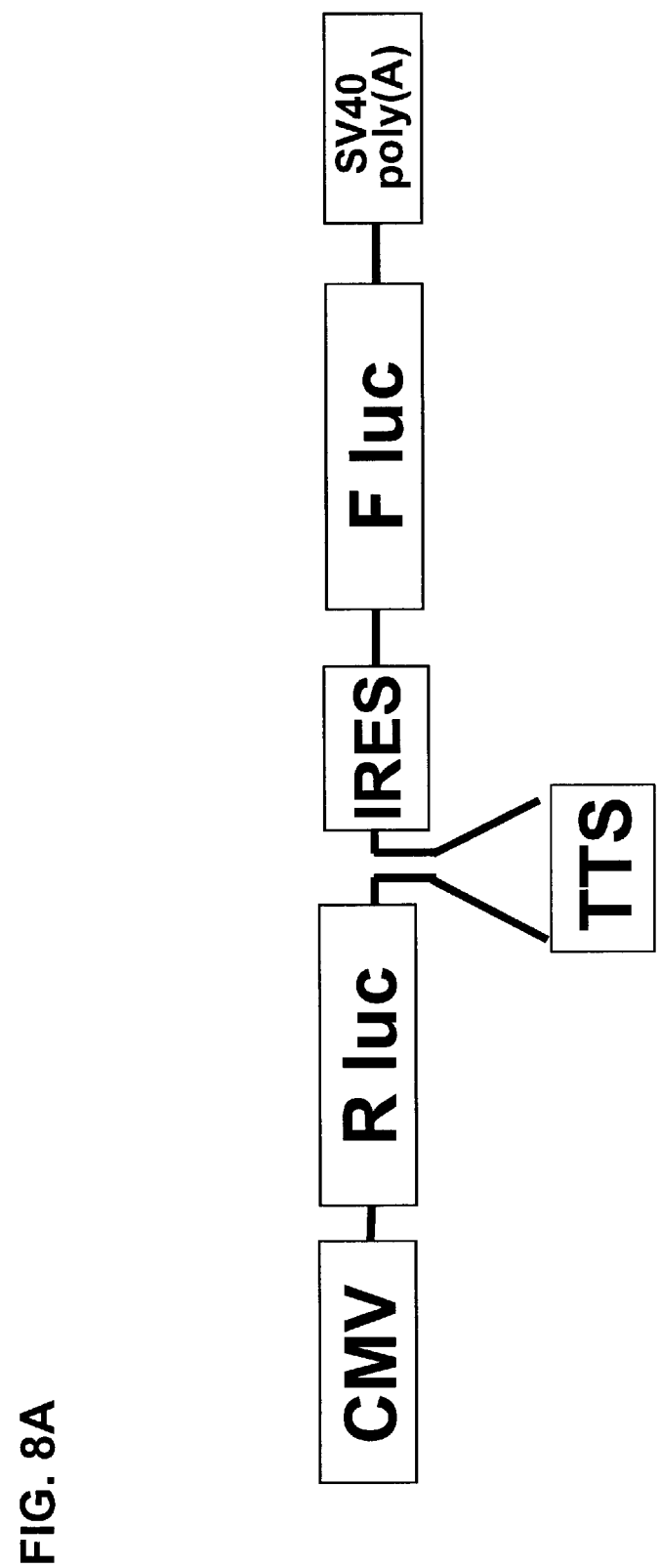
Figure 8B:
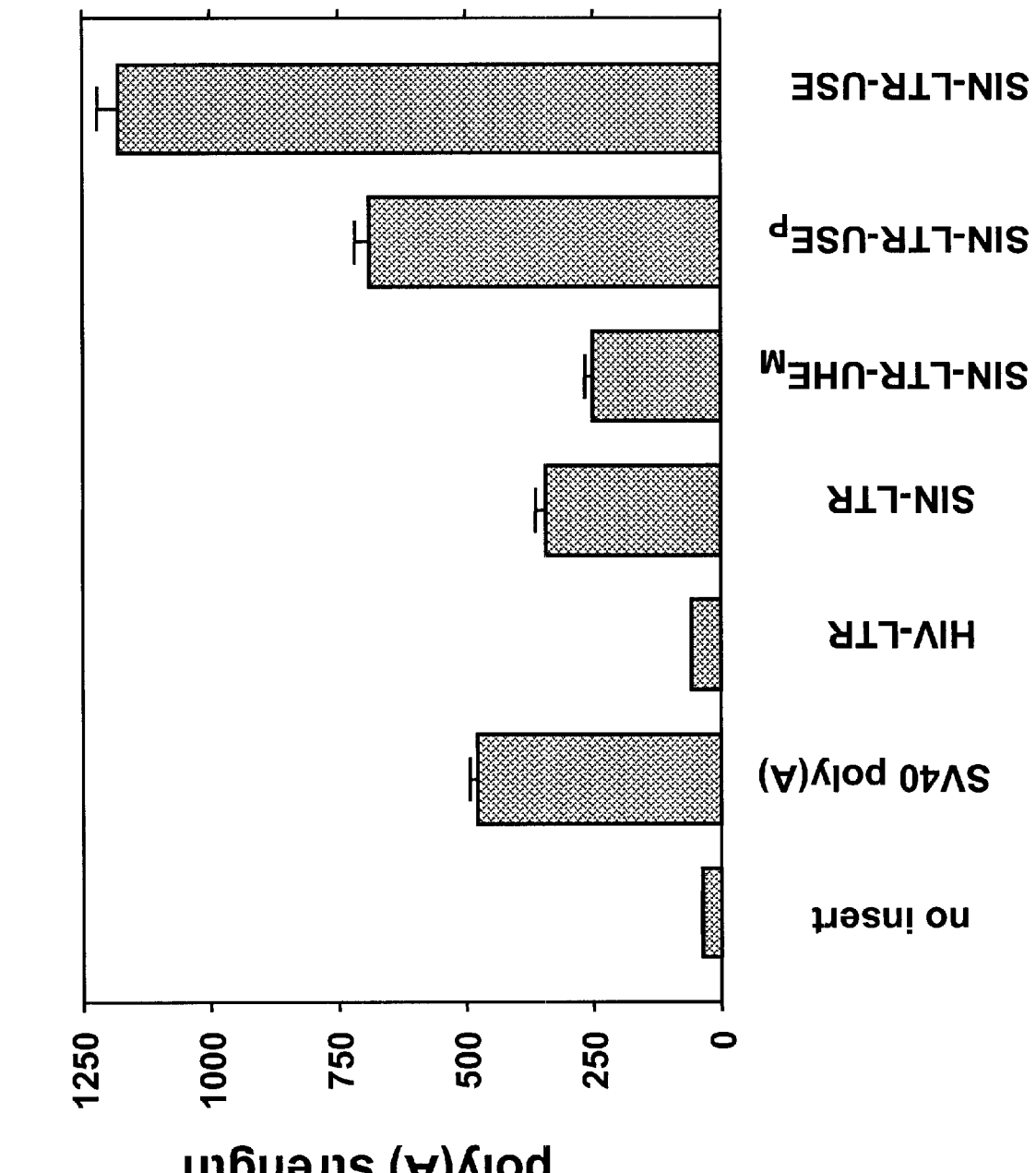

FIGS. 8A & 8B. Measuring Transcription Termination Efficiency.

FIG. 8A. Schematic of Polycistronic Expression Construct. CMV represents the cytomegalovirus promoter. R luc represents the Renilla luciferase coding sequence. TTS represents a Transcription Termination Structure. IRES represents an Internal Ribosome Entry Site. F luc represents the Firefly luciferase coding sequence. SV40 poly(A) represents SV40 polyadenylation signal.

FIG. 8B. Transcription Termination Activity

SIN-LTRs having the engineered transcription termination structures shown in FIGS. 7A and 7B are each inserted between two luciferase genes in the polycistronic expression construct at the TTS site. The constructs are transfected into 293T cells and the expression of R luc and F luc determined. The ratio of R luc/F luc reflects the efficiency/strength of the modified SIN-LTRs.

Figure 9:
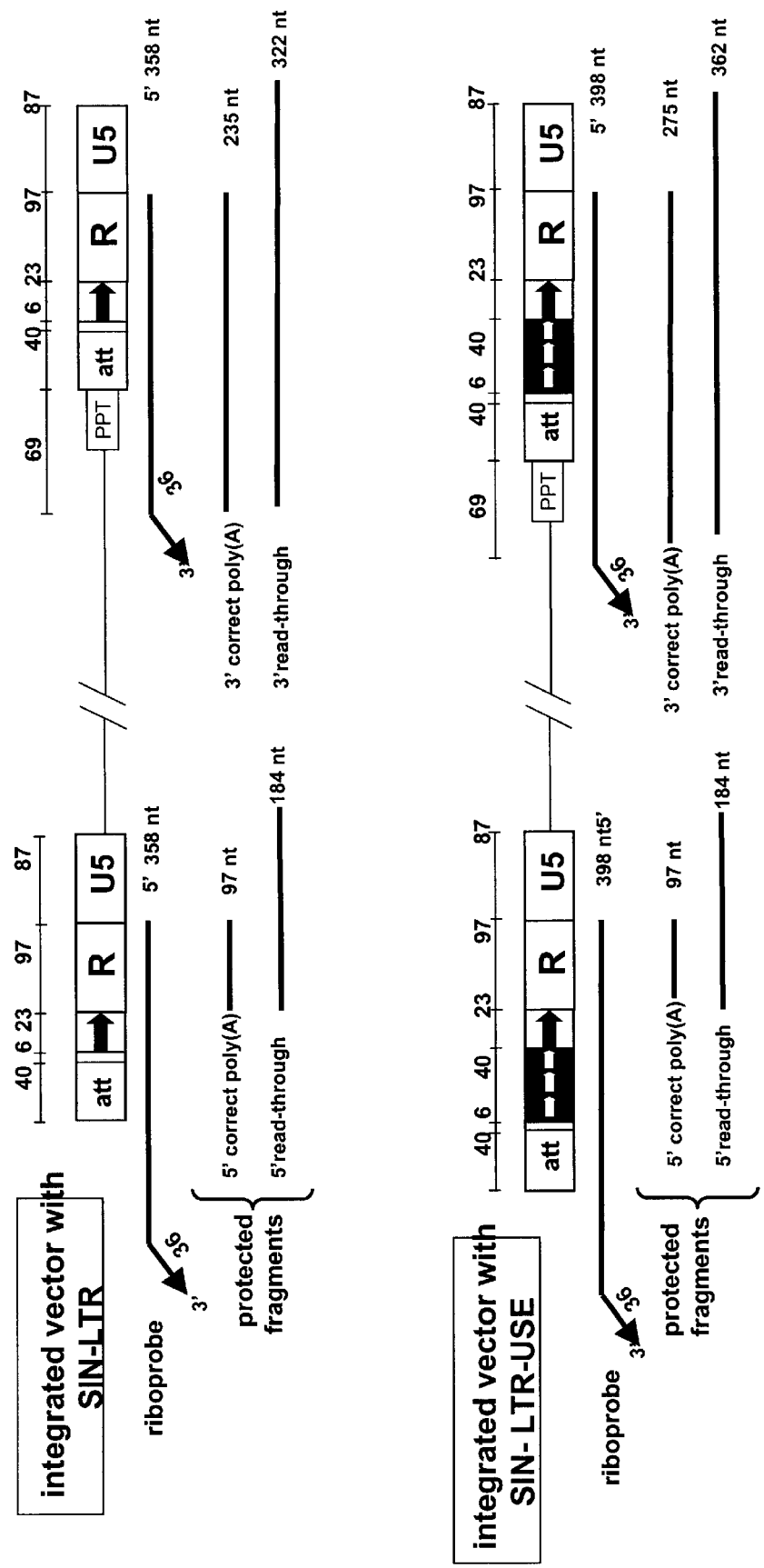

FIG. 9. Design of riboprobes for the analysis of 3' poly(A) efficiency by RNase protection assay.

The figure shows the arrangement of sequences in integrated vectors containing either a standard SIN-LTR (e.g., vectors pCSO, pCSO-MP), or the SIN-LTR-USE (e.g. vector pCSO-MP.USE). The position of the normal poly(A)/cleavage site is at the 3' R/U5 boundary. Specific riboprobes were designed for each vector to comprise the entire LTR region, the upstream polypurine tract (PPT) and an additional stretch of 36 nucleotide unrelated nucleotides 5' to the PPT. The sizes of the expected protected fragments are indicated. Transcripts that correctly terminate at the 3' R/U5 boundary can be distinguished from read-through transcripts because of the size differences, as indicated.

Figure 10:
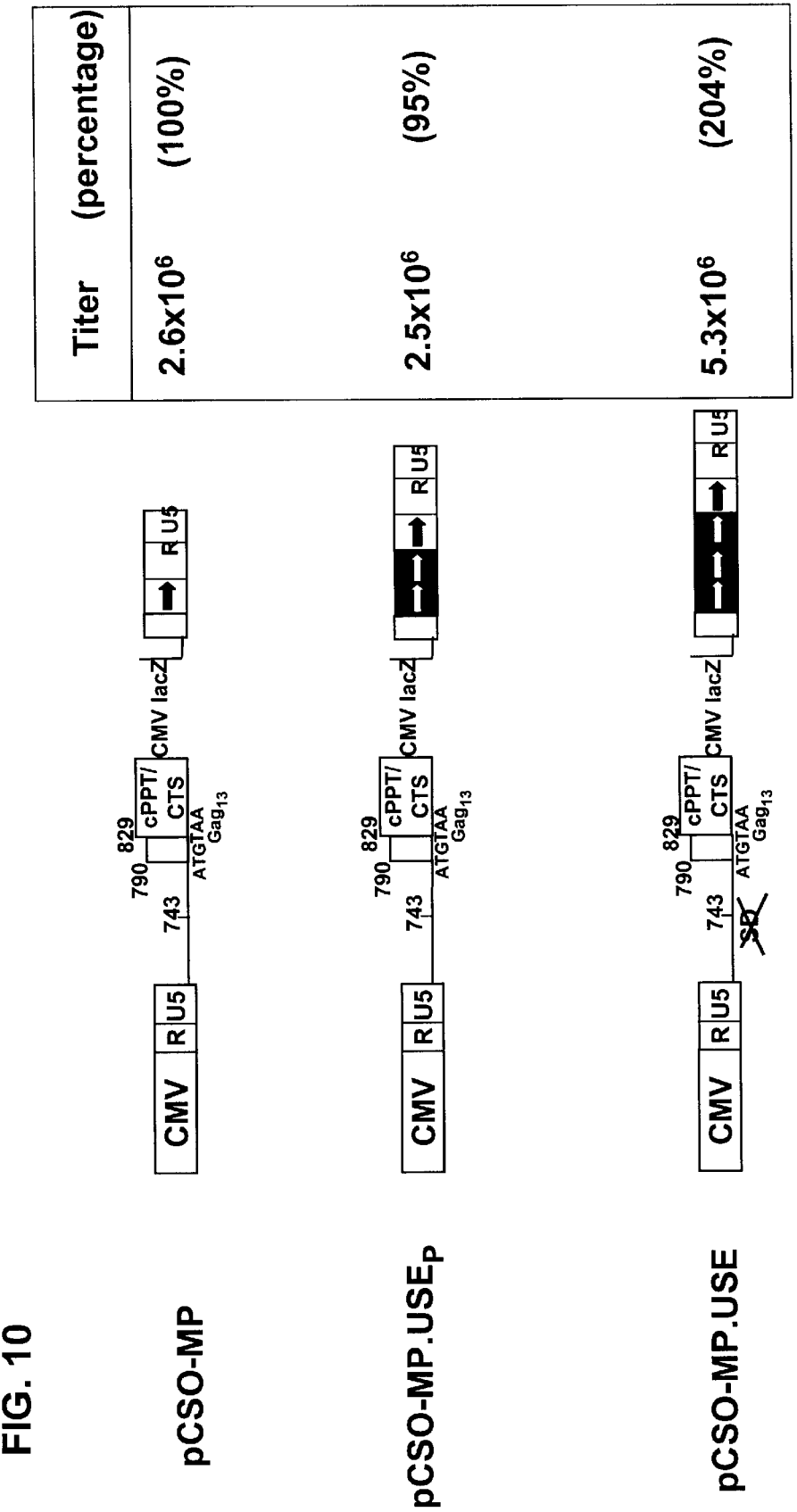

FIG. 10. Titer of Vectors Comprising USE Sequences.

Viral particles comprising the pCSO-MP, pCSO-MP.USE$_P$, pCSO-MP.USE, or pCSO-MP.UGE vector were generated by transient transfection and titered on 293T cells. Titers are shown as transducing units per ml.

DETAIL DESCRIPTION OF THE INVENTION
Retroviral Vectors of the Invention

The present invention provides retroviral vectors that have an enhanced 3' transcription termination structure. The vectors of the invention comprise a retroviral vector genome having a 5' LTR, a 3' LTR comprising a polyadenylation signal, and a packaging signal. The retroviral vector genome may be from a retrovirus including, but not limited to, Moloney murine leukemia virus, spleen necrosis virus, Rous sarcoma virus, Harvey sarcoma virus, avian leukosis virus, human immunodeficiency virus, myeloproliferative sarcoma virus, mammary tumour virus, human immunodeficiency virus, simian immunodeficiency virus, equine infectious anemia virus, feline immunodeficiency virus, bovine immunodeficiency virus, and visna virus. Preferably, the vectors comprise a retroviral vector genome that is replication defective. Typically, such a defect is due to a mutation and/or deletion of one or more viral structural and replication functions (e.g., gag, pol, env). Accordingly, vectors of the invention may be derived from replication defective retroviral vectors known in the art. Such vectors include, but are not limited to, retroviral vectors based on: Moloney murine leukemia virus, such as pCL (Naviaux et al., J Virol. 70:5701–5705 (1996)), G1XsvNA (Shubert et al., Curr. Eye Res. 16.656.662 (1997)), and pTIN414 (Cannon et al., J Virol. 70:8234–40 (1996)); and avian sarcoma/leukosis virus, such as RCASBP-M2C (Zheng et al., J Virol 73:6946–52 (1999)).

More preferably, vectors of the invention are derived from replication defective lentiviral vectors including, but not limited to, those based on: HIV-1, such as pHR'CMVIacZ, pHR'CMVIacZ SIN18, and pRRLPGK-GFP (Zufferey et al., J. Virol. 72:9873–9880 (1998)), LL-CG, CL-CG, LS-CG, CS-CG and CL-G (Miyoshi et al., J. Virol. 72, 8150–8157 (1998)), pV653CMVβ-gal (Gasmi et al., J Virol 73:1828–1834 (1999)), pTV (Iwakuma et al., Virology 261:120–132 (1999)), pH3Z, pH4Z, pH5Z (Kim et al., Virol. 72:811–816 (1998)); HIV-2 (Arya et al., Hum Gene Ther. 9:1371–80 (1998)); simian immunodeficiency virus, such as pVG (Schnell et al., Hum Gene Ther 11:439–47 (2000)); feline immunodeficiency virus, such as FIV-gal (Wang et al., J Clin Invest. 104:R55–62 (1999)), PTFIV (Johnston et al., J Virol 73:4991–5000 (1999)); equine infectious anemia virus, such as pONY2.10lacZ, pONY4.0Z (Mitrophanous et al., Gene Ther. 6:1808–18 (1999)); and bovine immunodeficiency virus (BIV), U.S. patent application Ser. No. 09/734,836, filed Dec. 12, 2000.

Most preferably, the vectors of the invention are derived from SIN lentiviral vectors, such as pHR'CMVIacZ SIN18 (Zufferey et al., J. Virol. 72:9873–9880 (1988)), LS-CG, CS-CG (Miyoshi et al., J. Virol. 72, 8150–8157 (1988)), SIN-W-PGK (Deglon et al., Hum Gene Ther. 11:179–190 (2000)), pVG (Schnell et al., Hum Gene Ther. 11:439–47 (2000)), and pTV (Iwakuma et al., Virology 261:120–132 (1999)).

The 5' LTR of the vectors may be an unmodified retroviral 5' LTR. That is, a native 5' LTR as it exists in a retrovirus. In a preferred embodiment, the endogenous U3 promoter of the 5' LTR has been inactivated by mutation and/or deletion and replaced with a heterologous promoter. The activity of the heterologous promoter may be constitutive, inducible or target cell-specific (i.e., expression is preferential or limited to one or several specific cell types and not or less so in other cell types). Useful heterologous promoters include, but are not limited to, CMV (Miyoshi et al., J. Virol. 72, 8150–8157 (1988)), Rous sarcoma virus promoter (Dull et al., J Virol. 72:8463–71 (1998)), tetracycline-inducible promoter (Hwang et al., J Virol. 71:712–831 (1997)).

The 3' LTR of the vectors may be an unmodified retroviral 3' LTR. In a preferred embodiment, the endogenous U3 promoter of the 3' LTR has been inactivated by mutation or deletion. In a more preferred embodiment, such inactivation is specific to the U3 promoter. That is, the inactivation does not adversely affect other structures, such as the att sequence and any endogenous UE, of the 3' LTR. In a most preferred embodiment, the promoter is inactivated by mutating or deleting sequences in the region that corresponds to about residues 9113 to 9506 of the pNL4-3 strain of HIV-1.

The vectors of the invention have an enhanced 3' transcription termination structure, which may comprise one or several UE sequences operably associated with the polyadenylation signal in the 3' LTR. The UE sequence may be a heterologous UE sequence or an additional copy of any endogenous UE sequence which may be present in the 3' LTR. In one embodiment, the 3' transcription termination structure comprises one or several heterologous UE sequences. In another embodiment, the 3' transcription termination structure comprises one or several additional copies of an endogenous UE sequence. In a futher embodiment, the 3' transcription termination structure comprises both heterologous and an additional copy of endogenous UE sequences.

The vectors of the invention may additionally comprise a microbial origin of replication and a microbial screenable or selectable marker for use in amplifying vector sequences in microbial cells, such as bacteria and yeast.

UE and Active Segments Thereof.

The vectors of the invention may comprise any UE. Preferably, the UE is from a eukaryotic or viral gene. Example viral UEs include, but are not limited to, those of SV40 virus (e.g., USE), cauliflower mosaic virus, HIV-1 (e.g., UHE), ground squirrel hepatitis virus (e.g. UGE), or equine infectious anemia virus UE (see FIG. 5). Examples of eukaryotic UEs include, but are not limited to, those of mammalian complement C2 and lamin B2 genes (see FIG. 5). In preferred embodiments, the retroviral vectors comprise the USE from SV40 or the UGE from ground squirrel hepatitits virus.

The vectors of the invention also may comprise an active segment of a UE. Such segment may be determined by routine experimentation using, for example, a transcription read-through assay. For example, such an assay may comprise a system for determining the relative expression levels of two reporter polypeptides encoded by a polycistronic expression construct, wherein the coding sequences of the reporter polypeptides are separated by a transcription termination structure and a downstream Internal Ribosome Entry Sequence (IRES). In particular, the expression construct may comprise the following elements in 5' to 3' direction: a transcriptional regulatory element (e.g., promoter or enhancer) that is active in the host cell, a coding sequence of the first reporter polypeptide, a first transcription termination structure, an Internal Ribosome Entry Sequence (IRES), a coding sequence of the second reporter, and optionally, a second transcription termination structure, wherein the first transcription termination structure comprises a polyadenylation signal. A schematic of such a construct is shown in FIG. 8A.

The transcriptional termination structures used in the construct may comprise the 3' untranslated region of a eukaryotic or viral gene. Preferably, the 3' untranslated region comprises an endogenous polyadenylation signal. In one embodiment, the transcription termination structure comprises a retroviral 3' LTR. In a preferred embodiment, the transcription termination structure comprises a modified 3' LTR, wherein the U3 promoter is inactivated by deletion or other means. In a more preferred embodiment, the transcription termination structure comprises a 3' LTR that is to be incorporated into a vector of the invention.

The activity of a UE segment may be determined by placing it upstream of the polyadenylation signal of the first transcription termination structure and determining whether the placement reduces transcription read-through past that structure. The orientation of the inserted UE segment to the polyadenylation signal in the 3' LTR should be the same as its orientation to the polyadenylation signal in the gene from which the UE segment was derived.

The UE segment may be inserted anywhere in the region between the coding sequence of the first reporter polypeptide and the polyadenylation signal of the first transcription termination structure. Preferably, the segment is inserted less than 100 nucleotides upstream of the polyadenylation signal. More preferably, the segment is inserted less than 50 nucleotides upstream of the polyadenylation signal. Most preferably, the segment is inserted less than 20 nucleotides upstream of the polyadenylation signal.

The read-through assay may be carried out by delivering DNA comprising the expression construct to a mammalian host cell using any method known in the art. Preferably, the host cell is from the same mammalian species as that of the intended target cell for the retroviral vector. More preferably, the host cell is from the same species and tissue type as the intended target cell for the retroviral vector. More preferably, the host cell is same as the intended target cell for the retroviral vector.

Read-through activity may be determined by comparing the level of the mRNA encoding both reporter polypeptides to that of the mRNA encoding just the first reporter polypeptide. Alternatively, the activity can be determined by comparing the relative levels of the two reporter polypeptides.

According to the invention, a UE segment is "active" and thus considered a "UE sequence" if it reduces read-through by at least about 10%, or enhances vector titer by at least 10% when it is operatively associated with the 3' LTR polyadenylation signal. According to the present invention, a UE sequence is at least 5 nucleotides in length.

Specific embodiments of UEs and active UE segments (i.e., UE sequences collectively) that may comprise vectors of the invention include, but are not limited to, the following:

a) The UE from SV40 (USE) comprising the sequence TTTATTTGTGAAATTTGTGATGCTATTGC-TTTATTTGTAA (SEQ ID NO:1); and all active segments thereof. In preferred embodiments, such segments comprise the sequence ATTTGTGA or ATTTG-TAA.

b) The equine infectious anemia virus UE comprising the sequence TTTGTGACGCGTTAAGTTCCTGTTTT-TACAGTATTATAAGTACTTGTGTTCTGACA ATT (SEQ ID NO:2); and all active segments thereof. In preferred embodiments, such segments comprise the sequence TTTGT, or TGTTTTT, or TTGTGTT.

c) The cauliflower mosaic virus UE comprising the sequence TGTGTGAGTAGTTCCCAGATAAGG-GAATTAGGGTTCTTATAGGGTTTCGCTCAT GTGTTGAGCATATAAGAAACCCTTAG-TATGTATTTGTATTTGTA (SEQ ID NO:5); and all active segments thereof. In preferred embodiments, such segments comprise the sequence TGTGTGAG-TAGTT (SEQ ID NO:3), or TGTGTTG, or TTAGTAT-GTATTTGTATTTGTA (SEQ ID NO:4).

d) The ground squirrel hepatitis virus UE (UGE) comprising the sequence TCATGTATCTTTTTCACCTGT-GCCTTGTTTTTGCCTGTGTTCCATGTC-CTACTGTT (SEQ ID NO:6); and all active segments thereof. In preferred embodiments such segments comprises the sequence TTTTT, or TTGTTTTTG, or TGT-GTT.

e) The adenovirus L3 UE comprising the sequence CCACTTCTTTTTGTCACTTGAAAAACAT-GTAAAAATAATGTACTAGGAGACACTTT (SEQ ID NO:8); and all active segments thereof. In preferred embodiments such segments comprises the sequence TTCTTTTTGT (SEQ ID NO:7).

f) The HIV-1 UE (also known as UHE) comprising the sequence CAGCTGCTTTTTGCCTGT (SEQ ID NO:11); and all active segments thereof. In preferred embodiments such segments comprise the sequence TTTTT.

g) The complement C2 UE comprising the sequence TTGACTTGACTCATGCTTGTTTCACTTTCA-CATGGAATTTCCCAGTTATGAAATT (SEQ ID NO:9); and all active segments thereof. In preferred embodiments such segments comprise the sequence TTGTTT or GTTATG.

h) The lamin B2 UE comprising the sequence ATTCG-GTTTTTAAGAAGATGCATGCCTAACGT-GTTCTTTTTTTTTTCCAATGATTT GTAATATA-CATTTTATGACTGGAAACTTTTTT (SEQ ID NO:10); and all active segments thereof. In preferred embodiments, such segments comprise the sequence TTTTT, or GTGTT, or TTTGT, or TTTTATG.

Operative Association of UE Sequence(s) with the 3' LTR Polyadenylation Signal

The vectors of the invention comprise one or several UE sequences that are operatively associated with the 3' LTR polyadenylation signal. Specifically, the operative association refers to an incorporation of UE sequence(s) that enhances transcriptional termination activity of the vector 3' LTR. Vectors having enhanced transcription termination may have various improved properties. Possible improvements include reduced transcription read-through into flanking vector or host sequences; increased production of vector RNA and/or vector encoded polypeptide; and higher vector titers in producer cells. According to the invention, a UE sequence is operatively associated with the 3' LTR polyadenylation signal if the incorporation effects more than about 10% improvement in any of these properties.

A UE sequence may be operatively associated with the 3' LTR polyadenylation signal by inserting the sequence at a vector site that is 5' upstream of the signal. The orientation of the inserted UE sequence to the polyadenylation signal should be same as its orientation to the polyadenylation signal in the gene from which the sequence was derived.

Preferably, the insertion site is less than about 500 nucleotides upstream of the signal, using the unmodified vector as a reference. More preferably, the site is less than about 100 nucleotides upstream. Even more preferably, the site is less than about 50 nucleotides upstream.

In a particularly preferred embodiment, the insertion is at a site in the U3 region of the 3' LTR. In a further preferred embodiment, such site is between the aft sequence and any endogenous UE sequence that may be present in the U3 region. In an even more preferred embodiment, a 3' LTR sequence between the att sequence and the R region containing some or all of the U3 promoter structure is deleted and the UE sequence is inserted at the deletion site. In a most preferred embodiment, such deletion span the region that corresponds to about residues 9113 to 9506 of the pNL4-3 strain of HIV-1 and the UE sequence is inserted into the deletion site.

Vectors Comprising a Plurality of UE Sequences

The vectors of the invention may comprise a plurality of UE sequences which are operably associated with the 3' LTR polyadenylation signal. The invention contemplates vectors comprising all possible combinations of multiple UE sequences. Example combinations include, but are not limited to: two or more heterologous UE sequences are identical or are derived from the same UE; two or more heterologous UE sequences that are derived from different UEs; two or more copies of the same endogenous UE sequence, two or more copies of different endogenous UE sequences; one or more heterologous UE sequence and one or more additional copies of an endogenous UE sequence.

Heterologous Genes and Coding Sequences

The vectors of the invention may be beneficially used to express desired gene products in mammalian cells and organisms. Accordingly, the vectors may additionally comprise one or more heterologous coding sequences, wherein such sequences are derived from sources other than the retroviral genome from which the vectors are derived.

In one embodiment, the heterologous coding sequences are inserted into the retroviral backbone, preferably between the 5' and 3' LTRs, such that they are operably associated with the 5' LTR promoter. Where such insertions lead to production of polycistronic mRNA comprising the heterologous coding sequences, it may be advantageous to also operatively associate each heterologous coding sequence with an IRES in order to achieve efficient translation of each sequence.

In another embodiment, the heterologous coding sequences are each operably associated with an individual promoter to form expression constructs, and such constructs are inserted into the retroviral backbones, preferably between the 5' and 3' LTRs. The expression constructs may comprise promoters that are constitutive, inducible, tissue-specific, or cell-cycle specific. Examples of useful promoters include, but are not limited to, the SV40 promoter, CMV promoter, adenovirus promoters, B19 parvovirus promoters, histone promoter, pol III promoter, and beta-actin promoters.

Diverse gene products may be expressed using vectors of the invention. They include polypeptides, structural RNAs, anti-sense RNAs and ribozymes. In one embodiment, the vectors of the invention comprise and express one or more heterologous sequences encoding therapeutic polypeptides. Example therapeutic polypeptides include cytokines, growth factors, hormones, kinases, receptors, receptor ligands, enzymes, antibody polypeptides, transcription factors, blood factors, and artificial derivatives of any of the foregoing.

In another embodiment, the vectors of the invention comprises and express one or more heterologous sequences encoding negative selectable markers. The negative selectable markers may be cytotoxins that directly or indirectly inhibit or kill a host cell. Examples of "direct" cytotoxins include the active moieties of cholera and botulism toxins. In a preferred embodiment, the vectors of the invention comprise and express one or more heterologous sequences encoding indirect cytotoxins. The indirect cytotoxins by themselves are not toxic but achieve cellular inhibition by interacting with another agent. An example is HSV-thymidine kinase (TK) which is non-toxic but can activate drugs like ganciclovir into a toxic nucleotides that kill mammalian cells.

Vector Particles

Infectious retroviral particles comprising vectors of the invention may be produced by methods well known in the art. For example, vector particles can be produced by transfecting a packaging cell expressing in trans the required retroviral replication functions, such as Gag/Pol and Env proteins. Gag and Pol provide viral structural and enzymatic components and Env functions to target vector particles to target cells. Env function can comprise an envelope protein from any retrovirus or a fusion or spike protein from another enveloped virus (e.g., VSV G protein) or any molecule that binds a specific cell surface receptor.

The infectious vector particles of the invention may be used to express heterologous coding sequences in mammalian cells and organisms. In one embodiment, an effective dose of infectious vector particles comprising a heterologous coding sequence is administered directly to the mammalian organism to achieve transduction of target cells within the organism. In another embodiment, mammalian cells are transduced in vitro with the such vector particles and the transduced cells are then administered in vivo to a host. Preferably, the infectious vector particles of the invention are used to express heterologous coding sequences in primates and primate cells. More preferably, the vector particles of the invention are used to to express heterologous coding sequences in humans and human cells.

EXAMPLE

Introduction

This example demonstrates the construction of novel retroviral vectors that have a highly efficient transcription termination structure in their 3' LTRs. This was accomplished by inserting USE sequences derived from the SV40 late polyadenylation signal into the 3' LTR U3 region of a self-inactivating (SIN) lentiviral vector. During reverse transcription, the 3' LTR U3 region is copied into both vector LTRs, such that both the 5' and 3' LTRs of the integrated vector contain this USE-SIN configuration. Vectors comprising the novel LTR structures have enhanced polyadenylation efficiency, reduced read-through transcription from the integrated provirus, and increased vector titer by at least 2-fold when compared to the parental SIN retroviral vector pCSO-MP.

Methods and Results

Retroviral Vectors

The parental SIN vector pCSO-MP comprises a lentiviral backbone and represents an improvement over conventional SIN vectors such as pCSO which is similar to those previously described (e.g. Miyoshi et al., J. Virol. 72:8150–7 (1988)) (FIG. 6). pCSO contains 2100 nucleotides of HIV-1 genomic sequences. In pCSO-MP, the HIV-1 sequences have been reduced to 835 nucleotides. The key features of this vector compared to previously described SIN vectors are the deletion of all of the HIV-1 splice sites and env sequences, a significant reduction in the amount of the gag open-reading frame and the insertion of the central polypurine tract/central termination sequence (cPPT/CTS) into pCSO-MP (FIG. 6). These modifications greatly reduce the extent of homologous sequence overlap between the vector and sequences encoding packaging components, and thereby reduces the risk of generation of a replication-competent retrovirus (RCR) through homologous recombination, while maintaining optimal vector function. Derivatives of pCSO-MP comprising various transcriptional termination constructs are prepared and their properties examined.

Transcription Termination Constructs

Several transcription termination constructs comprising SIN-LTR modified with various UE sequences are prepared using standard recombinant DNA methods and approaches. One construct SIN-LTR-USE comprises a 40 nucleotide sequence containing the complete USE of SV40, which has three core AUUUGUPuA elements. Another construct SIN-LTR-USE$_P$ comprises a partial USE, having only two core elements. The third construct SIN-LTR-UHE$_M$ comprises the HIV-1 putative minor polyadenylation enhancer having the sequence TTTCCGCTGGGACTTT (SEQ ID NO:12) (UHE$_M$). The fourth construct SIN-LTR-UGE comprises the complete 56 nucleotide long UGE sequence from ground squirrel hepatitis B virus. In each construct, the UE sequence is inserted between the integration attachment site (Masuda et al., J. Virol. 72:8396–8402 (1998)) and the endogenous HIV-1 upstream enhancer (UHE) (Valsamakis et al., Mol Cell Biol. 12:3699–3705 (1992)) of the 3' LTR of pCSO-MP. These insertions are facilitated by the engineering of a Xho I restriction site at the junction of the att and the UHE in the U3 region of SIN-LTR. The structures of these constructs are shown in FIGS. 7A and 7B.

Transcription Read-Through Assay

The activities of these transcription termination constructs are assessed using a transcription read-through assay based on the polycistronic expression cassette shown in FIG. 8A. The transcription termination constructs are inserted between two reporter genes, renilla luciferase (R luc) and firefly luciferase (F luc) and the amount of R luc and F luc activity is measured following transfection of plasmids comprising the expression cassette into 293T cells. The R luc and F luc activities are determined using a luciferase assay kit (Promega). The presence of an internal ribosome entry site (IRES) sequence in the expression cassette allows for F luc expression, even though it is the second coding sequence on the mRNA. In this configuration, the expression of F luc is inversely related to the efficiency by which transcription is terminated by the inserted construct. In addition, the expression level of the first reporter gene, R luc, reflects the overall stability/translatability of its mRNA, which is also influenced by the strength of the inserted construct. Taken together, these two different effects of an inserted termination construct combine to alter the ratio of expression of the two luciferase reporter genes. The activities of the constructs can be compared based on their effects on the ratio of R luc:F luc expressed (i.e., a construct having a high ratio has enhanced termination activity as compared to a construct having a lower ratio).

The aforementioned assay shows that the transcription termination structure in SIN-LTR-USE is a stronger polyadenylation signal than either the native HIV-1 LTR, or even the wild-type SV40 late polyadenylation signal, which is considered to be one of the strongest signals known. The addition of a complete USE increases the polyadenylation strength of the SIN-LTR by about 3-fold, while the addition of only two of USE's AUUUGUPuA elements in SIN-LTR-USEP enhances polyadenylation strength by about 2-fold. The addition of the HIV-1 putative minor enhancer (SIN-LTR-UHE$_M$) decreases polyadenylation efficiency. These results are summarized in FIG. 8B.

RNase Protection Assay

RNase protection assays are used to analyze the ratios of correctly terminated vector transcripts versus read-through transcripts for a variety of SIN-derived vectors having different transcription termination structures in their LTRs. Labeled RNA probes are prepared for each vector 3' LTR configuration (FIG. 9) and used to probe vector-derived transcripts in 293T cell populations containing the various vectors. These assays show that the SIN-LTR polyadenylation signal in vector pCSO-MP generates both correctly polyadenylated and read-through transcripts with approximately the same efficiency. In contrast, insertion of the USE or USE$_P$ elements into the SIN-LTR at the att and UHE boundary substantially increases the amount of 3' processing at the correct polyadenylation site and correspondingly reduces the amount of read-through transcripts. (data not shown)

Vector Titers

The complete and a partial USE and the complete UGE are inserted into the 3' LTR of vector pCSO-MP to create vectors pCSO-MP.USE, pCSO-MP.USE$_P$ and pCSO-MP.UGE, respectively. Vector particles are generated by co-transfecting plasmids comprising these vectors with replication helper plasmids pCMVΔR8.71 and pMD.G into 293T cells as described (Naldini et al., Science 272:263–267 (1996)). Vector supernatants produced by the transfected cells are titered on 293T cells. These analyses shows that vector pCSO-MP.USE gave vector titers that are at least twice as high as the standard SIN-LTR vector, pCSO-MP (FIG. 10). The ability to increase vector titer is not only the property of USE, since UGE in vector pCSO-MP.UGE increased vector titers by almost 2-fold. It is known that higher steady-state levels of mRNA result from processing by strong polyadenylation signals. Thus it is likely that the 3' SIN-LTR-USE or 3' SIN-LTR-UGE configurations confer higher stability to vector transcripts in the producer cell, which in turn results in higher vector titers.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

The disclosures of all patents, patent applications, publications (including published patent applications), depository accession numbers, and database accession numbers are incorporated herein by reference to the same extent as if each patent, patent application, publication, depository accession number, and database accession number were specifically and individually incorporated by reference.

What is claimed is:

1. A retroviral vector comprising:
   a) a 5' LTR;
   b) a 3' LTR comprising a polyadenylation signal; and
   c) one or more heterologous upstream enhancer (UE) sequences selected from the group consisting of SE ID NOs:1–11 and active segments thereof, operatively associated with said polyadenylation signal.

2. The retroviral vector of claim 1 which comprises more than one heterologous UE sequence, at least two of which are the same.

3. The retroviral vector of claim 1 which comprises several more than one heterologous UE sequence, at least two of which are different.

4. The retroviral vector of claim 1 which comprises one or more additional copies of endogenous UE sequences.

5. The retroviral vector of claim 4 which comprises more than one additional copy of an endogenous UE sequence.

6. The retroviral vector of claim 1, wherein at least one of said one or more heterologous UE sequences, is in said 3' LTR.

7. The retroviral vector of claim 1, wherein at least one of said one or more heterologous UE sequences is in the U3 region of the 3' LTR.

8. The retroviral vector of claim 1, wherein said 3' LTR has no functional U3 promoter.

9. The retroviral vector of claim 8, wherein said 3' LTR comprises a deletion of U3 promoter sequence.

10. The retroviral vector of claim 9, wherein at least one of said one or more heterologous UE sequences, is at the U3 promoter deletion site.

11. The retroviral vector of claim 1, wherein said one or more heterologous UE sequences are selected from the group consisting of: SEQ ID NO:1 or an active segment thereof, SEQ ID NO:3 or an active segment thereof, SEQ ID NO:11 or an active segment thereof, SEQ ID NO:6 or an active segment thereof, and SEQ ID NO:2 or an active segment thereof.

12. The retroviral vector of claim 1, wherein said one or more heterologous UE sequences is a UE sequence comprising ATTTGTGA or ATTTGTAA.

13. The retroviral vector of claim 1, wherein said one or more heterologous UE sequences is a UE sequence comprising ATTTGTGAAATTTGTGATGCTATTGCTT-TATTTGTAA (SEQ ID NO: 1).

14. The retroviral vector of claim 1, wherein said one or more heterologous UE sequences are selected from the group consisting of: SEQ ID NO:9 or an active segment thereof, and SEQ ID NO:10 or an active segment thereof.

15. The retroviral vector of claim 1, which comprises a lentiviral sequence.

16. The retroviral vector of claim 1, wherein said 3' LTR comprises an endogenous UE sequence.

17. The retroviral vector of claim 1, wherein said 5' LTR comprises a heterologous promoter inserted in the U3 region.

18. The retroviral vector of claim 17, wherein 5' LTR comprises a deletion of the endogenous U3 promoter sequence.

19. The retroviral vector of claim 1, which comprises a heterologous coding sequence which is 3' downstream of said 5' LTR and 5' upstream of said 3' LTR.

20. The retroviral vector of claim 19, wherein said heterologous coding sequence encodes a therapeutic polypeptide.

21. The retroviral vector of claim 19, wherein said heterologous coding sequence encodes a negative selective marker.

22. An in vitro cell comprising the retroviral vector of claim 1.

23. The cell of claim 22 which is a mammalian cell.

24. The cell of claim 23 which is a human cell.

25. An infectious retroviral particle produced by the cell of claim 24, wherein said cell is a producer cell.

26. A method for expressing a heterologous coding sequence in an in vitro cell comprising delivering to said cell the retroviral vector of claim 19.

27. The method according to claim 26, wherein said heterologous coding sequence encodes a therapeutic polypeptide.

28. The method according to claim 26, wherein said heterologous coding sequence encodes a negative selective marker.

29. A method for expressing a heterologous coding sequence in an in vitro cell comprising delivering to said cell an infectious retroviral particle comprising the retroviral vector of claim 19.

30. The method according to claim 29, wherein said heterologous coding sequence encodes a therapeutic polypeptide.

31. The method according to claim 29, wherein said heterologous coding sequence encodes a negative selective marker.

* * * * *

SEQUENCE LISTING

<160> NUMBER OF SEQ ID NOS: 15

<210> SEQ ID NO 1
<211> LENGTH: 40
<212> TYPE: DNA
<213> ORGANISM: Simian virus 40

<400> SEQUENCE: 1
tttatttgtg aaatttgtga tgctattgct ttatttgtaa          40

<210> SEQ ID NO 2
<211> LENGTH: 59
<212> TYPE: DNA
<213> ORGANISM: Equine infectious anemia virus

<400> SEQUENCE: 2
tttgtgacgc gttaagttcc tgtttttaca gtattataag tacttgtgtt ctgacaatt    59

<210> SEQ ID NO 3
<211> LENGTH: 13
<212> TYPE: DNA
<213> ORGANISM: Cauliflower mosaic virus

<400> SEQUENCE: 3
tgtgtgagta gtt          13

<210> SEQ ID NO 4
<211> LENGTH: 22
<212> TYPE: DNA
<213> ORGANISM: Cauliflower mosaic virus

<400> SEQUENCE: 4
ttagtatgta tttgtatttg ta          22

<210> SEQ ID NO 5
<211> LENGTH: 98
<212> TYPE: DNA
<213> ORGANISM: Cauliflower mosaic virus

<400> SEQUENCE: 5
tgtgtgagta gttcccagat aagggaatta gggttcttat agggtttcgc tcatgtgttg    60
agcatataag aaacccttag tatgtatttg tatttgta          98

<210> SEQ ID NO 6
<211> LENGTH: 56

<210> SEQ ID NO 6
<211> LENGTH: 56
<212> TYPE: DNA
<213> ORGANISM: Ground squirrel hepatitis virus

<400> SEQUENCE: 6
tcatgtatct ttttcacctg tgccttgttt ttgcctgtgt tccatgtcct actgtt      56

<210> SEQ ID NO 7
<211> LENGTH: 10
<212> TYPE: DNA
<213> ORGANISM: Adenovirus type 2

<400> SEQUENCE: 7
ttctttttgt      10

<210> SEQ ID NO 8
<211> LENGTH: 56
<212> TYPE: DNA
<213> ORGANISM: Adenovirus type 2

<400> SEQUENCE: 8
ccacttcttt ttgtcacttg aaaaacatgt aaaaataatg tactaggaga cacttt      56

<210> SEQ ID NO 9
<211> LENGTH: 55
<212> TYPE: DNA
<213> ORGANISM: Homo sapiens

<400> SEQUENCE: 9
ttgacttgac tcatgcttgt ttcactttca catggaattt cccagttatg aaatt      55

<210> SEQ ID NO 10
<211> LENGTH: 88
<212> TYPE: DNA
<213> ORGANISM: Homo sapiens

<400> SEQUENCE: 10
attcggtttt taagaagatg catgcctaac gtgttctttt tttttccaa tgatttgtaa      60 tatacatttt atgactggaa actttttt      88

<210> SEQ ID NO 11
<211> LENGTH: 18
<212> TYPE: DNA
<213> ORGANISM: Human immunodeficiency virus type 1

<400> SEQUENCE: 11
cagctgcttt ttgcctgt      18

<210> SEQ ID NO 12
<211> LENGTH: 16
<212> TYPE: DNA
<213> ORGANISM: Human immunodeficiency virus type 1

<400> SEQUENCE: 12
tttccgctgg gacttt      16

<210> SEQ ID NO 13
<211> LENGTH: 14
<212> TYPE: DNA
<213> ORGANISM: Simian virus 40

<400> SEQUENCE: 13
ccattataag ctgc      14

-continued

```
<210> SEQ ID NO 14
<211> LENGTH: 62
<212> TYPE: DNA
<213> ORGANISM: Artificial Sequence
<220> FEATURE:
<223> OTHER INFORMATION: Fig. 7A SV40 late poly(A)

<400> SEQUENCE: 14
tttatttgtg aaatttgtga tgctattgct ttatttgtaa ccattataag ctgcaataaa      60
ca                                                                    62

<210> SEQ ID NO 15
<211> LENGTH: 111
<212> TYPE: DNA
<213> ORGANISM: Artificial Sequence
<220> FEATURE:
<223> OTHER INFORMATION: Fig. 7A SIN-LTR-USE poly(A)

<400> SEQUENCE: 15
actggaaggg ctaattcact cccaacgaag acaagatatc ctcgagttta tttgtgaaat      60
ttgtgatgct attgctttat ttgtaagcag ctgcttttg cctgtactgg g               111
```